United States Patent [19]

Mabie et al.

[11] 4,431,451

[45] Feb. 14, 1984

[54] DENTAL MATERIAL

[75] Inventors: Curtis P. Mabie, Thurmont; Daniel L. Menis, Gaithersburg, both of Md.

[73] Assignee: American Dental Association Health Foundation, Chicago, Ill.

[21] Appl. No.: 341,682

[22] Filed: Jan. 22, 1982

Related U.S. Application Data

[63] Continuation-in-part of Ser. No. 237,746, Feb. 24, 1981, abandoned, which is a continuation-in-part of Ser. No. 120,823, Feb. 12, 1980, abandoned, which is a continuation-in-part of Ser. No. 32,934, Apr. 22, 1979, abandoned.

[51] Int. Cl.$^3$ .................................................. C09K 3/00
[52] U.S. Cl. ........................................ 106/35; 501/12; 501/18; 501/21; 501/66; 501/67; 501/141; 433/202; 433/199; 433/222
[58] Field of Search ...................... 106/35; 501/12, 18, 501/21, 66, 67, 141; 314/32, 934, 120, 823, 157, 182, 237, 746

[56] References Cited

U.S. PATENT DOCUMENTS

| | | | |
|---|---|---|---|
| 3,759,683 | 9/1973 | Dislicti .................................... | 106/52 |
| 3,782,982 | 1/1974 | Pierson et al. ......................... | 106/75 |
| 3,929,439 | 12/1975 | Pierce .................................... | 106/74 |
| 3,973,970 | 8/1976 | Marbie ................................... | 106/35 |
| 4,217,264 | 8/1980 | Marbie et al. ......................... | 106/35 |
| 4,361,654 | 11/1982 | Ohmura et al. ....................... | 501/21 |

OTHER PUBLICATIONS

Mukherjee et al., *A Comparative Study of "Gels" and Oxides Mixtures as and Starting Materials for Nucleation and Crystallization of Silicate Glasses,* 11 (1976), pp. 341-355.
Fripiat et al., *Hydroxyl Content in Silica Gell "Aerosil",* 66 J. Phys. Chem., 800-805 (1962).
Kuczynski et al., Formation of Glasses by Sintering, 54 J. Amer. Cer. Soc., 51 (1971).
McLean et al., *The Reinforcement of Dental Porcelain Ceramic Oxides,* 116 Brit. Dent. J., 251-64 (1965).
Southan., *Strengthening Modern Dental Porcelan by Ion Exchange,* 15 Aust. Dent. J., 507-510 (1970).
Ishitobi et al., *Fabrication of Transulcent $Al_2O_3$ by High Pressure Sintering,* 56 Cer. Soc. Bull. 10-16 (1977).
MacCulloch, *Advances in Dental Ceramics,* 124 Brit. Dent. J., 361-65 (1968).
Yoldas, B. E., *Alumina Gels That Form Porous Transparent $Al_2O_3$,* Jour. of Materials Science, vol. 10, pp. 1856-1860 (1975).
Uytterhoeven et al., *Le frittage des gels de silic.,* Silicate Industriels, pp. 241-246, Oct. 1962.
Yoldas, *A Transparent Porous Alumina,* Amer. Cer. Soc. Bull., pp. 286-290 (1975).
McCarthy et al., *Gel Route to Homogeneous Glass Preparation: 11 Gelling and Desiccation,* Jour. Amer. Ceramic Soc., pp. 639-640 (Dec. 1971).
Marbie, C. P. et al., *Microporous Glassy Fillers for Dental Composite,* Journal of Biomedical Research, vol. 12, 435-472 (1978).
McCarthy, G. J., *Preliminary Study of Low Temperature, "Glass Fabrication" From Noncrystalline Silicas,* Jour. of the Amer. Ceramic Society, vol. 54, No. 12, pp. 637-638 (Dec. 1971).
Luth, W. C., *Gel Preparation of Starting Materials for Hydrothermal Experimentation,* The Amer. Mineralogist, vol. 50, pp. 255-258 (Feb. 1965).
Kitazawa et al., *Determination of Mass Transport Mechanism of Rutile by Sinusoidal Profile Decay Method,* vol. 60, No. 7-8, J. of the Amer. Cer. Soc., pp. 350-363, Aug. 1977.
*Microporous Glassy Fillers for Dental Cement,* Marbie et al., Apr. 1976.
Lynch et al., Engineering Properties of Ceramics, Jun. 1966.

*Primary Examiner*—Theodore Morris
*Attorney, Agent, or Firm*—Allegretti, Newitt, Witcoff & McAndrews, Ltd.

[57] ABSTRACT

Dentures, dental glazes or coatings, reconstructive jacket-crowns and inlays and restorative constructions over metal or preformed alumina substrates are fabricated from a dental porcelain frit prepared by a gel route.

28 Claims, No Drawings

DENTAL MATERIAL

The invention described herein was made in the course of work under a grant or award from the Department of Health, Education and Welfare.

This application is a continuation-in-part of co-pending application Ser. No. 237,746, filed Feb. 24, 1981 which is a continuation-in-part of application Ser. No. 120,823, filed Feb. 12, 1980 which is a continuation-in-part of application Ser. No. 32,934, filed Apr. 22, 1979 all abandoned.

BACKGROUND OF THE INVENTION

Field of the Invention and Description of the Prior Art

The present invention relates to the area of procelain frits, their preparation and use, and especially to dental procelain frits. Dental porcelain frits are useful as the raw material for preparation of procelain denture teeth, reconstructive jacket-crowns and inlays, and restorative constructions over metal or preformed alumina substrates.

Despite the considerable efforts of dental manufacturers, current commercial dental procelains are characterized by high fabrication costs, significant fabrication difficulties and severe performance problems. The fact that the highest paid worker in a dental laboratory is usually the ceramist suggests the difficulty of dental porcelain fabrication. The properties of dental porcelain which result in these fabrication difficulties include (1) firing shrinkage, (2) flow deformation or slumping, (3) stress buildup in the porcelain body (usually as a result of mechanical incompatibilities originating at the porcelain-to-metal interface), (4) flaws and incipient cracks commonly generated within the porcelain by grinding, and (5) warp.

Firing shrinkage is the single greatest factor complicating the processing of restorative dental procelains and is a factor in the failure of porcelain-to-metal bonds. The firing shrinkage of various porcelains under differing conditions ranges from as low as 27 to as high as more than 40 volume percent. Repeated rapid firing and cooling to add to the porcelain and thus compensate for this shrinkage subject the dental construction to repeated thermal shock which results in uneven stress buildup in the porcelain and contributes to stress accumulation in the total metal-ceramic unit.

Flow deformation, the second important problem in porcelain fabrication, is apparent in the edge rounding, central massing and nonuniform shrinkage of the porcelain. These characteristics make shoulder construction and marginal adaptation difficulat and contribute to the difficulty of porcelain inlay and jacket-crown fabrication. Ordinally, the central massing problem can only be reduced by scoring the construction. To compensate for flow deformation effects, it has been common to overbuild, especially shoulders, which in turn requires grinding back and re-firing.

Flow deformation has been minimized to some extent in a few commercial body or dentin porcelains, but apparently not effectively with enamel and incisal porcelains. One of the most commercially successful porcelains for metal-ceramic constructions (Ceramco, Johnson & Johnson) exhibits severe edge rounding caused by flow deformation. This rounding may be alleviated by proper application of a liquid additive consisting of a water solution of silica sol and small amounts of fluxing agents. See U.S. Pat. No. 3,973,970. The additive there described constitutes a minor proporation of what is other wise a traditionally prepared porcelain. However, it would be preferable to have form retention during firing inherent in the raw porcelain powder.

Stress buildup in the porcelain may be caused by a number of factors and may result in weakening or even failure of the porcelain-to-metal bond. Excessive basemetal oxidation can cause formation of thick surface layers of refractory oxides of chromium, aluminum and manganese causing failure in adherence of porcelain to metal. The firing of porcelain on metal at temperatures at which metal flow deformation occurs can result in a casting of poor fit. Ultimately, most stresses at the porcelain-to-metal interface appear attributable to the differential thermal contraction which occurs between porcelain and metal on cooling after firing. The stress effects induced in the metal-ceramic by variations in thermal history and dimensional compensations make it imperative to simplify and abbreviate porcelain fabrication operations, particularly the number of fires. This can only be accomplished if the problems which dictate an increase in the number of fires, i.e., firing shrinkage, flow deformation, and, to lesser extent, warp, are in turn minimized.

The overbuilding of commercial porcelain to compensate for flow deformation also generates the need for machining the fired porcelain. Grinding of dental porcelain introduces flaws which may or may not be satisfactorily healed by glazing and refiring. Susceptibility to failure introduced by cracks, flaws and brittleness is a serious problem with aesthetic dental porcelains. Even with careful fabrication, the tensile strength of ground, unstressed translucent porcelain is not particularly high for a ceramic material, even though it exceeds the strength of tooth dentin.

Current commercial dental porcelain frits are prepared from cyrstalline oxides, e.g., feldspar, quartz and boric oxide, by a process that requires complex mineral beneficiation, milling and blending procedures followed by high temperature fusions and calcinations involving remilling and reheating. The fusion step is followed by the supercooling of silicate liquids. As the liquid supercools, the composition passes through immiscibility domes where the viscosities are sufficiently low to permit phase separation. The resulting commercial dental porcelain frits are not compositionally homogeneous on a microscale. They contain quartz, relict (or partially digested) feldspar and other phases in various degrees of digestion and formation. It is believed that uniform fluxing of all porcelain size fractions aids in form retention. However, such iniform fluxing is impossible when the fluxing constituents are not homogeneously distributed, as is the case with commercial dental porcelain frits.

Furthermore, when porcelains prepared by traditional high temperature fusions are over-fired, they "age" and become too translucent, develop too high a gloss, may discolor, exhibit excessive flow deformation, and, if severely overfired, become too brittle and weak and dull in appearance.

Attempts have been made to remedy some of the problems encountered wth existing dental porcelains. Aluminous porcelains have been prepared and are said to improve rupture and compressive strength and to inhibit crack propagation. See McClain & Hughes, "The Reinforcement of Dental Porcelain With Ceramic Oxides," 116 *Brit. Dent. J.* 251-64 (1965). However, due to excess opacity, these materials are suitable only for the construction of cores of crown and inlay porcelain and are not useful as body or dentin porcelain in metal-ceramic restorations.

To strengthen porcelains, the introduction of compression into the ceramic via ion exchange with molten alkali nitrate has been suggested, but appears too complicated for the extreme simplicity demanded in the dental laboratory. See Southan, "Strengthening Modern Dental Porcelain by Ion Exchange," 15 *Aust. Dent. J.* 507-510 (1970). Also, sintered translucent aluminas are extremely strong with tensile strength easily in excess of 760 kg.cm$^2$. See Linch, Ruderer & Duckworth, "Engineering Properties of Selected Ceramic Materials," *American Ceramic Society* 5, 4, 1–9 and 5, 4, 1–17 (1966). However, the prolonged firing times and high processing temperature required in the preparation of sintered translucent aluminas preclude their use except as preforms. See Ishitobi, Shimada & Korzumi, "Fabrication of Translucent Al$_2$O$_3$ by High Pressure Sintering,"56 *Cer. Soc. Bull.* 10-16 (1977).

Glass-ceramics have been experimentally developed for dental restorations, and the strengths are very much greater than those of ordinary porcelains. See MacCulloch, "Advances in Dental Ceramics," 124 *Brit. Dent. J.* 361-65 (1968). However, the procedure involves casting molten glass into molds and heat-treating to generate the glass-ceramic. From a process point of view, this technique with its complicated "pyroceraming" to generate color shade appears too difficult for restorative use.

The instant invention makes available a new type of dental porcelain frit and dental porcelain prepared from that frit which avoid many of the problems of prior art compositions prepared by traditional fusion techniques. The inventive porcelain frit is characterized in that it is prepared by a gel route. Thus, the final porcelain construction is derived from an amorphous precursor, rather than from crystalline oxides. Preparation of dental porcelain by a gel route is believed to be an entirely new field of endeavor. An area of research which is somewhat related, but clearly distinct, is the general investigation of gel route prepared glasses.

Investigation of compositions formed by acidification followed by dehydration of glasses with oxide components of Li$_2$O, Na$_2$O, K$_2$O, Rb$_2$O, MgO, CaO, SrO, BaO, PbO, Ga$_2$O$_3$, Fe$_2$O$_3$, La$_2$O$_3$, TiO$_2$, ZrO$_2$, and ThO$_2$ has shown that these components are more homogeneous than the best glasses obtained by the usual techniques of melting solid oxide constituents, and that fewer meltings are required to achieve homogeneity. See Roy, "Gel Route to Homogeneous Glass Preparations," 54 *J. Amer. Cer. Soc.* 639-40 (1971). See also Roy, "Rational Molecular Engineering of Ceramic Materials," 60 *J. Amer. Cer. Soc.* 350-63 (1977). It is known that glass preparation by the gel route is faster, less labor intensive, and requires less energy than is needed for preparing glass from traditional crystalline oxide materials and that fully dessicated gels from which all water and nitrogen oxides have been removed by heating can be melted and cooled to yeild clear glasses 100° to 200° C. below the temperatures required for standard batch materials. See McCarthy & Roy, "Gel Route to Homogeneous Glass Preparation: II. Gelling and Dessication," 54 *J. Amer. Cer. Soc.* 639-40 (1971). See also Kuczynski & D'Silva, "Formation of Glasses by Sintering," 54 *J. Amer. Cer. Soc.* 51 (1971).

Other workers have confirmed that glasses made from gels in the system SiO$_2$—Al$_2$O$_3$—La$_2$O$_3$—Zro$_2$ are more homogeneous than those made from crystalline oxide mixtures. See Mukherjee, Zarzycki & Traverse, "A Comparative Study of 'Gels' and Oxide Mixtures as Starting Materials for the Nucleation and Crystallization of Silicate Glasses," 11 *J. Mat. Sci.* 34–355 (1976). This reference is directed to the investigation of properties of gel-prepared glasses and glass-ceramics. The gels are fused by complete melting at very high temperature (e.g., 2,000° C.) and are then permitted to cool. It has been shown that the effective poor size of alumina gels heat treated to 500° C. and above increases as the surface area decreases. It appears that the sintering between primary particles which causes reduction in microporosity does not reduce greatly the total pore volume. See Yoldas, "Transparent Porous Alumina," *Amer. Cer. Soc. Bull.* 286-90 (1975). Additional work in the field of gel prepared glasses is exemplified by U.S. Pats. Nos. 3,929,439; 3,759,683; 3,782,982; German Pat. No. 2,128,845; German Pat. No. 2,128,980; and by Fripiat & Vytterhoeven, "Hydroxyl Content in Silica Gel 'Arerosil', 66 *J. Phys. Chem.* 800–05 (1962); Vytterhoeven, Hellinckx & Fripiat, "Le Frittage des Gels de Silica," *Silicates Industriels* 241-46 (1962); Yoldas, "Alumina Gels That Form Porous Transparent Al$_2$O$_3$,"10 *j. Mast. Sci.* 1856;14 60 (1975); Luth & Ingamells, "Gel Prepartion of Materials for Hydrothermal Experimentation,"50 *The Amer. Mineral,* 255-58 (1965); McCarthy, Roy & McKay, "Preliminary Study of Low-Temperature 'Glass' Fabrication," 54 *J. Amer. Cer. Soc.,* 636-38 (1971). For advances in the area of gel-prepared microporous glassy fillers for dental resin composites, see Mabie & Menis, "Microporous Glassy Fillers for Dental Composites," 12 *J. Biomed. Mats. Res.* 435-72 (1978), now the subject of U.S. Pat. Nos. 4,217,264 and 4,306,913.

SUMMARY OF THE INVENTION

All the limitations of existing dental porcelain and its obvious alternatives indicate the need for the development of new materials. Plastics may require less skill to fabricate, but their oral performance is known to be poor. Therefore, a better performing porcelain or glass-ceramic appears to be the material required.

The present invention relates to a novel porcelain frit, a method of preparing this frit and products prepared from the frit.

It is an object of this invention to lower the cost of porcelain frit preparation by process simplification, by improving ease of quality control, and by reducing manufacturing space requirements.

It is a further object to employ a new method of frit formation which results in porcelain frits having a partial glass-ceramic state in which bonding is more crystalline and thereby tougher and stronger with attendant improved porcelain strength and mechanical performance.

It is also an object of this invention to produce more homogeneous porcelain frits which fuse at lower temperatures without increased oral solubility of the fabricated porcelain.

Other objects of this invention include:

(1) decreasing the firing time for porcelain maturation, (2) widening the porcelain firing range by enhancing form retention and retarding the development of excessive translucency or dullness and the firing out of coloring agents, (3) permitting the preparation of frits with a greater variety of oxide components and both metallic and non metallic dispersed phase constituents which will allow the fabrication of porcelains with precisely tailored optical opacification, thermal expansion, strength and bondability to metallic bridgework, and (4) allowing the precise sizing of frit particles to minimize firing shrinkage.

Another object of this invention is the preparation of dental porcelain articles such as metal-ceramic and total porcelain jacket-crown and inlay restorations and denture teeth from the porcelain frits of the invention.

The thrust of this invention is toward improving dental porcelain by utilizing frit grain prepared by a gel route. Emphasis is upon development of porcelain products with less technique sensitivity and variation.

These and other objects of the invention are accomplished by the use of improved dental porcelain frits prepared by a gel route. Specifically, sols comprising alumina, silica and various fluxes and other additives are mixed, gelled and ordinarily precalcined, comminuted and then calcined and optionally melted into a dense frit which may be subsequently milled to an appropriate size.

More specifically, in making porcelain frit by a gel route, a gel is prepared first from a mixture comprising alumina and silica sols with significant proportions of dissolved boric, sodium, and potassium oxides. Commonly, lithium oxide is substituted in varying proportions for potassium and sodium oxides. Minor proportions of zinc, tin, calcium, magnesium, zirconium, phosphorus and other oxides may be solubilized and added to the sol system.

Large additions of nitric acid and commonly methanol, and, in a few mixtures, small additions of acetic acid, are preferably used to peptize the sol systems. Alternatively, the gels may be peptized by solubilized carbonate anions. Gelling of the mixed sols is accomplished by a slow volatilization of the solvent. The gel is then heated in one or more steps to calcination temperatures. More specifically, after the formation of a rigid gel prepared from an acid-stabilized sol, the gel is precalcined, or heated at a moderate temperature, to drive off additional loosely bound volatiles such as water, alcohol and acid. In this context, the term "moderate temperature" refers to a temperature between about 90 and about 1,000° C., preferably between about 90 and about 700° C. Most preferably, the first sub-step in this precalcination takes the form of heating at approximately 90 to 200° C. for up to 40 to 60 hours. During this time the gel is further dried, hardened and made dense. To complete the precalcination, hardened "cured" gel is then heated at temperatures ranging from about 400 to about 700° C.

Precalcined frit is ground and then calcined at temperatures ranging up to about 1400 or 1500° C., but commonly no higher than 1,000° C. If the calcined frit is bloated or porous, that is, has a low density, it is reground and recalcined. Since the carbonate-stabilized, as opposed to acid-stabilized, sol does not require defuming, the heating to calcination and the calcination itself may be carried out as one continuous process step.

In certain cases, following calcination, the frit is melted in the neighborhood of the lowest temperature which will provide a bubble-free quenched melt.

The frit is subsequently ground to form the raw porcelain which can be fired to form porcelain denture teeth, reconstructive jacket-crowns and inlays, and restorative constructions over metal or preformed alumina substrates.

DESCRIPTION OF THE PREFERRED EMBODIMENTS

The acid peptized sols from which the porcelain frits of the present invention are preferably prepared preferably comprise a mixture of 55–70% silicon dioxide, 5–18% aluminum oxide, and solubilized oxides of boron ($B_2O_3$, 0–10%) sodium ($Na_2O$, 2–15%), potassium ($K_2O$, 2–18%), and lithium ($Li_2O$, 0–18%), and of calcium, magnesium, barium, strontium, zinc, tin, phosphorus, cesium, rubidium, yttrium, ytterbium, samarium, lanthanum, titanium, tantalum, zirconium, terbium, thullium, cerium, europium and scandium (individually ranging from 0–5%). (All percents are by weight and are based on the total solid oxide content of the sol. Eventual volatilization of all nitrogen oxides, water, alcohol, and pyrolyzed matter such as acetic acid is assumed.) Nitric acid, sometimes methanol, and infrequently acetic acid, additions are preferably used to peptize a water-based sol system containing these oxides. Nitric acid also acts to effect frit densification during precalcination and to completely oxidize organic mattfer introduced into the sol.

Alkali and zirconium oxides may be solubilized from a carbonate together into concentrated nitric acid solutions. Zinc may be solubilized as the nitrate, and tin may be introduced as a methanol solution of stannic chloride pentahydrate. Boric and phosphorus oxides may be added to the sol systems as water solutions of boric acid and monoammonium phosphate, respectively. One weight percent solutions of boric and phosphorus oxides are convenient for this purpose. Also, very small amounts of sodium, lithium, and calcium fluorides may be added to the starting sol system to aid frit densification during both precalcination and calcination.

Most of the solubilized alumina and silica is preferably added as a chloride-stabilized sol of 4 weight percent $Al_2O_3$ and 26 weight percent $SiO_2$. (This is commonly available as Ludox 130 M, DuPont de Nemours & Co., Wilmington, Del.) If a greater solubilized alumina content is needed, a chloride-stabilized 22 weight percent $Al_2O_3$ sol (5025 Hammill & Gillespie, New York, NY) is added to the sol. Greater silicato-alumina ratios may be obtained by adding an 18 weight percent $SiO_2$-ethyl orthosilicate solution (available as Silbond H-4, Stauffer Chemical Co., New York, NY). The solubilized silica and alumina are preferably mixed directly with the nitric acid solution which contains in a dissolved form all the remaining frit constituents.

It is possible to add alumina to the acid systems in the form of aluminum nitrate. If a totally water-based system is desired with a higher pH near neutrality, alumina and sodium may be added as sodium aluminate and silica as a potassium silicate. It is believed that additional required alumina may also be added to near neutral water systems as aluminum nitrate. Furthermore, in these water systems, additional silica may be added as the various sodium metasilicates to sodium stabilized colloidal silicas. Potentially, ammonium stabilized silicas may be used.

In some formulations, ultra-fine silica produced by flame reactions (Cab-O-Sil, Cabot Corp., Boston, Mass.) may be introduced into the fully-mixed sol as a substitute for all or part of the total solubilized silica. Such additions appear to increase the firing range and the maturation temperature of the resulting porcelain.

Soluble nitrates of calcium, magnesium, barium, strontium, cesium, rubidium, yttrium, ytterbium, samarium, lanthanum and scandium may be dissolved in distilled water and added to the sol.

Rare earth oxide phosphors, including the oxides of terbium, thullium, yttrium, ytterbium, cerium, samarium and europium may be employed singly or in a combination appropriate for the given color shade desired to provide the finished porcelain teeth or restorative reconstructions with a nonradioactive enhancing fluorescence. Preferably, the rare-earth oxides when employed are incorporated in amounts ranging from 0.005 to 0.5% by weight in the calcined raw porcelain frit. The rare earth oxides may be dissolved either directly as the oxide ($(metal)_2O_3$) in a nitric acid solution and then added to the sol solution, or may be solubilized as the nitrate. In instances in which the oxide is insoluble, it may be solubilized from material subjected to borax, or sodium and/or potassium carbonate fusions.

As an alternative to acid peptizing of the sols, the gels may be peptized by solubilized carbonate anions. A specific illustration of this technique appears in Example 5.

To create porcelains with special properties, fine particles of quartz, potash feldspar, nepheline syenite, beta alumina, pyrex and fused quartz or silica fiber, hydrated unfused alumina, glass frits, unfused alumina, fused alumina, mica (particularly lepidolite mica), high-fusing porcelain frit and also various metal powders with low vapor pressures, e.g. titanium, aluminum, silicon and tantalum, may be introduced into the sol. Such constituents can be dispersed more easily and effectively into a sol than into a viscous molten frit, and without the need for high temperature melting. Certain additives, such as mica, could not be incorporated into traditionally prepared porcelain frit because they would undergo decomposition at the temperature involved. It is thought that the use of low vapor pressure metals such as titanium and tantalum in bonding and opacifying porcelains will not result in porcelain discoloration and possibly will result in their complexing with vaporized constituents from the alloy. This complexing may inhibit the discoloration of porcelain by high vapor pressure alloy constituents, e.g, copper, manganese and silver. These particles are kept in full suspension during gellation by constant stirring. As the viscosity of the gelling mixture increases, so does the ease of maintaining this particle dispersion.

Gellation is accomplished by solvent volatilization. After a gel prepared from an acid-stabilized sol attains rigidity, it is ordinarily precalcined. The gel is dried or dessicated, for instance in a drying oven or on top of a hot plate, preferably at temperatures of about 90 to about 200° C. for up to 40–60 hours. To complete precalcination, the dried gel is heated or defumed, for example in a muffle furnace, preferably at about 400° to about 700° C., most preferably by defuming for one hour each at temperatures of 500°, 600° and 700° C. Precalcination temperatures may, however, reach as high as 1,000° C. During precalcination, nitrogen oxides and bound water, along with other flux constituents, particularly traces of fluorides and chlorides (less than 0.5%), promote the reduction of microporosity and thereby frit densification. The precalcined frit is then ordinarily comminuted prior to calcination. Stage-grinding of the precalcined frit in a mullite mortar through 40- to 100-mesh is preferred.

The comminuted frit is subjected to calcination at temperatures ranging from about 700° to about 1,400° or 1,500° C., preferably from about 700° to about 1,000° C., to form a calcinate. The preferred procedure involves the stepwise heating of the precalcined frit, most preferably at successive 25° C. intervals for one hour each from an initial temperature of 725° C., with retention times at maximum calcination temperature varying from 1 to 61 hours. Calcination is continued until a dense high-biscuit-type gloss is obtained. If the fritted mass becomes bloated, it is reground and recalcined. Commonly, up to four calcinations may be required to prepare satisfactory frits; in some instances, up to ten may be required. Heating of the precalcined frit to temperatures in the neighborhood of 1,500° C. results in incomplete or partial melting of the material, rather than in a complete melting in the sense of complete dissolution of all the phases.

Optionally, the calcined frit may then be melted at approximately the lowest temperature which will provide a bubble-free quenched melt. Preferably, this step is accomplished by melting the calcined frit in platinum foil by holding at the peak temperature for thirty minutes, where the peak temperature is determined by heating in steps of 50° C., holding for thirty minutes, quenching in water, and examining for the appearance of fine bubbles. When the quenched melt appears free of fine bubbles, operations cease.

Frits are then processed by techniques known in the art to prepare the final porcelain product. The frits are comminuted once again, preferably by milling, ordinarily with pebbles, to sizes suitable for the construction of restorative or denture tooth porcelains, then coated on a metal or ceramic substrate or made as a total porcelain jacket crown or inlay. Frits may also be molded to shapes in the green state, extracted from the molds and fired to make denture teeth. The careful milling of the frit to obtain particles of varying sizes reduces firing shrinkage. In comparison with commercially available dental porcelain frits, the inventive frits have low firing temperatures, generally below 960° C. and even lower in many instances.

The following examples illustrate the practice of certain specific embodiments of the present invention.

EXAMPLE 1 (COMPARATIVE EXAMPLE)

Method

Porcelain frits are prepared as follows. A sol is prepared with solubilization of the components by the preferred means described above resulting in mixtures with compositions as listed in Table I. Gelling of the mixed sols is accomplished by slow volatilization of solvent from a 500 to 600 cc slurry placed in a 6-inch diameter crystallization dish on a hot plate. During volatilization and gellation, constant stirring is used to maintain suspension. After the formation of a rigid gel, heat treatment on the hot plate is continued at approximately 150° to 200° C. for up to 24 hours. To complete precalcination, hardened gel is then heated in a muffle furnace at temperatures ranging from 450° to 500° C. for one hour. The door of the muffle furnace is left slightly open to allow the escape of nitrogen oxides. Precalcined frit is stage-ground in a mullite mortar through 40-, 100- or 140-mesh and then placed in a porcelain crucible for calcination. Calcination takes place at temperatures as high as 960° C. for time periods ranging from 2/3 to almost 150 hours. (See Table V.) Any frits which are bloated or porous, that is, have a low density, are reground through any of these mesh sizes and recalcined. For the preparation of porcelain test pieces, raw porcelain frit is prepared by stage grinding through 100-, 140-, and 200-mesh and by prolonged dry and wet pebble milling.

Fillers are added to the sol in certain batches to aid in dispersion strengthening, optical opacification, and, in the case of metallic additions, to promote bonding to the metal substrate construction.

TABLE I

Raw Porcelain Compositions, mole %

| Batch No. | Frit Fraction SiO₂ Solubilized Cab-O-Sil | Al₂O₃ | B₂O₃ | K₂O | Na₂O | NaF | Li₂O | LaF | ZrO₂ | CaO | MgO | P₂O₅ | ZnO | SnO₂ | Filler Fraction, Weight % |
|---|---|---|---|---|---|---|---|---|---|---|---|---|---|---|---|
| C-5 | 72.325 | 9.842 | 7.562 | 5.224 | 4.646 | — | — | | | | | | | | |
| 6 | 72.325 | 9.842 | 7.962 | 5.224 | 4.646 | — | — | | | | | | | | |
| 14 | 72.257 | 9.927 | 7.955 | 5.220 | 4.641 | — | — | | | | | | | | |
| 15 | 72.477 | 9.909 | 7.865 | 5.161 | 4.588 | — | — | | | | | | | | |
| 16 | 71.846 | 9.822 | 7.797 | 5.116 | 4.549 | — | 0.869 | | | | | | | | |
| 18 | 71.846 | 9.822 | 7.797 | 5.116 | 4.549 | — | 0.869 | | | | | | | | |
| 19 | 71.227 | 9.738 | 7.725 | 5.072 | 4.510 | — | 1.724 | | | | | | | | |
| 20 | 71.240 | 9.739 | 7.730 | 5.073 | 4.510 | — | 0.862 | | 0.207 | 0.637 | | | | | |
| *C-20 | 71.651 | 9.795 | 7.775 | 5.102 | 4.536 | — | 0.651 | | 0.104 | 0.385 | | | | | |
| 21 | 71.772 | 9.812 | 7.788 | 5.111 | 4.543 | — | 0.864 | | 0.105 | — | | | | | |
| 22 | 71.823 | 9.792 | 7.772 | 5.100 | 4.535 | — | 0.433 | | 0.104 | 0.640 | | | | | |
| 23 | 71.314 | 9.750 | 7.739 | 5.078 | 4.515 | — | 0.863 | | 0.104 | 0.638 | | | | | |
| 24 | 72.130 | 9.861 | 7.828 | 5.136 | 4.567 | — | 0.436 | | 0.104 | — | | | | | |
| 25 | 72.068 | 9.853 | 7.820 | 5.135 | 4.563 | — | 0.436 | | 0.042 | 0.128 | | | | | |
| *C-26 | 72.477 | 9.909 | 7.845 | 5.161 | 4.588 | — | — | | — | — | — | | | | |
| 27 | 71.786 | 9.814 | 7.791 | 5.111 | 4.545 | — | 0.869 | | 0.084 | 0.319 | 0.316 | | | | |
| 28a | 71.315 | 9.750 | 7.739 | 5.078 | 4.515 | — | 0.863 | | 0.104 | 0.319 | 0.316 | | | | |
| 28b | 71.315 | 9.750 | 7.729 | 5.078 | 4.515 | — | 0.863 | | 0.104 | 0.317 | 0.630 | 0.138 | | | |
| 29a | 70.933 | 9.697 | 8.210 | 5.051 | 4.491 | — | 0.429 | | 0.104 | 0.317 | 0.630 | 0.138 | | | |
| 29b | 70.933 | 9.697 | 8.210 | 5.051 | 4.491 | — | 0.429 | | 0.104 | 0.317 | 0.630 | | | | |
| 30a | 71.475 | 9.772 | 8.273 | 5.090 | 4.525 | — | 0.866 | | — | — | — | | | | |
| 30b | 71.475 | 9.772 | 8.273 | 5.090 | 4.525 | — | 0.866 | | — | — | — | | | | |
| 31a | 70.665 | 11.744 | 7.664 | 5.029 | 4.470 | — | 0.427 | | — | — | — | | | | |
| 31b | 72.161 | 9.865 | 7.830 | 5.133 | 4.568 | — | 0.437 | | — | — | — | | | | |
| 32 | 70.232 | 9.601 | 8.130 | 5.000 | 4.453 | — | 0.850 | | 0.102 | 0.628 | 0.624 | 0.273 | 0.106 | | |
| 33a | 71.527 | 9.779 | 7.762 | 5.093 | 4.528 | — | 0.433 | | 0.104 | 0.320 | 0.318 | 0.028 | 0.108 | | |
| 33b | 71.527 | 9.779 | 7.762 | 5.093 | 4.528 | — | 0.433 | | 0.104 | 0.320 | 0.318 | 0.028 | 0.108 | | |
| 34b | 72.337 | 9.889 | 7.850 | 5.151 | 4.580 | — | — | | — | 0.129 | 0.064 | — | — | | |
| 35b | 72.161 | 9.865 | 7.830 | 5.138 | 4.568 | — | 0.437 | | — | — | — | — | — | | |
| 36b | 69.621 | 9.518 | 9.066 | 5.408 | 4.701 | — | 1.686 | | — | — | — | — | — | | |
| 37 | 69.190 | 9.459 | 9.010 | 4.927 | 4.380 | — | 1.675 | | 0.101 | 0.309 | 0.307 | 0.538 | 0.104 | | |
| 38 | 30.964 | — | — | — | — | — | 21.947 | | — | — | — | — | 47.089 | — | |
| 39 | 31.483 | 11.069 | — | — | — | — | 31.428 | | — | — | — | — | 26.020 | | |
| 40 | 36.948 | 12.991 | — | — | — | — | 19.524 | | — | — | — | — | 30.537 | | |
| 41 | 77.02 | 10.11 | 7.80 | 7.88 | 4.99 | — | — | | | | | | | | |
| 42 | 72.83 | 9.94 | 11.28 | 5.28 | 4.151 | — | — | | | | | | | | |
| 43 | 49.42 | 25.59 | 15.80 | 0.77 | 3.82 | — | — | | | | | | | | |
| 44 | 52.15 | 13.03 | 7.95 | — | — | — | 19.02 | | | 9.12 | | | | | |
| 45 | 62.17 | 4.88 | 7.73 | — | 4.11 | — | 25.00 | | | — | | | | | |
| 46 | 71.15 | 11.95 | 7.73 | 5.06 | 4.11 | — | — | | | — | | | | | |
| | 35.514 35.636 | | | | | | | | | | | | | | |
| 47 | 70.67 00.00 70.67 | 11.87 | 7.68 | 5.03 | 4.08 | — | 0.67 | | | | | | | | |
| 48 | 70.45 00.00 70.45 | 11.83 | 7.66 | 5.01 | 4.07 | — | 0.68 | 0.30 | | | | | | | |
| 49 | 70.31 17.561 52.749 | 11.81 | 7.64 | 5.00 | 4.06 | 0.20 | 0.68 | 0.30 | | | | | | | |

TABLE I-continued

Raw Porcelain Compositions, mole %

| Batch No. | Frit Fraction SiO2 Solubilized Cab-O-Sil | Al2O3 | B2O3 | K2O | Na2O | NaF | Li2O | LaF | ZrO2 | CaO | MgO | P2O5 | ZnO | SnO2 | Filler Fraction, Weight % |
|---|---|---|---|---|---|---|---|---|---|---|---|---|---|---|---|
| 50 | 70.372 35.180 35.182 | 11.519 | 7.646 | 5.004 | 4.063 | — | 0.670 | — | — | — | — | 0.426 | — | — | |
| 51 | 70.012 0.000 70.912 | 11.759 | 7.606 | 4.984 | 4.043 | 0.200 | 0.670 | 0.300 | — | — | — | 0.426 | — | — | |
| 52 | 69.942 0.000 69.942 | 11.749 | 7.596 | 4.974 | 4.043 | 0.200 | 0.670 | 0.300 | — | — | — | 0.426 | 0.100 | — | |
| 53 | 62.410 39.321 3.089 | 4.885 | 7.890 | — | — | — | 24.814 | — | — | — | — | 0.426 | 0.10 | — | |
| 54 | 62.162 32.841 9.321 | 4.886 | 7.950 | — | — | — | 25.082 | — | — | — | — | — | — | — | |
| 56 | 62.170 46.827 15.543 | 4.890 | 7.950 | — | — | — | 25.000 | — | — | — | — | — | — | — | |
| 56a | 62.408 43.686 18.722 | 4.899 | 7.413 | — | — | — | 23.181 | — | 0.064 | — | — | 2.035 | — | — | |
| 56b | 62.408 43.666 18.722 | 4.999 | 7.413 | — | — | — | 23.181 | — | 0.064 | — | — | 2.035 | — | — | |
| 57 | 57.113 34.267 22.844 | 9.297 | 5.273 | — | — | 1.406 | 12.897 | 11.437 | — | — | — | 2.577 | — | — | |
| 58 | 69.148 58.776 10.372 | 9.454 | 5.005 | 4.924 | 4.377 | — | 2.454 | — | 0.101 | — | — | 0.538 | — | — | |
| 59 | 69.990 45.497 24.493 | 10.015 | 5.998 | — | — | — | 9.797 | 0.200 | — | — | — | — | — | — | |
| 60 | 70.630 60.035 10.595 | 11.758 | 7.673 | 5.035 | 4.476 | — | 0.428 | — | — | — | — | — | — | — | |
| 61 | 69.669 62.702 6.967 | 11.703 | 7.566 | 4.954 | 4.417 | 0.100 | 0.668 | 0.299 | — | — | — | 0.425 | 0.199 | — | |
| 62 | 70.066 56.069 14.017 | 10.012 | 10.012 | — | — | — | 9.011 | 0.200 | 0.137 | — | — | 0.341 | 0.200 | — | |
| 63 | 68.989 58.637 10.352 | 9.631 | 8.957 | 4.916 | 4.366 | 0.100 | 2.190 | — | — | — | — | 0.644 | 0.109 | 0.100 | |
| 64 | 60.004 62.095 6.609 | 9.618 | 8.959 | 4.916 | 4.368 | — | 2.489 | — | — | — | — | 0.645 | — | — | 10.363 (Pyrex fiber) |
| 65 | 68.994 58.642 10.364 | 9.632 | 8.957 | 4.917 | 4.366 | — | 2.487 | 0.200 | — | — | — | 0.645 | — | — | |
| 66 | 69.005 62.096 6.909 | 9.618 | 8.959 | 4.916 | 4.368 | — | 2.488 | — | — | — | — | 0.645 | — | — | 10.366 (Feldspar) |
| 67 | 69.009 65.561 3.448 | 9.607 | 8.962 | 4.918 | 4.369 | — | 2.489 | — | — | — | — | 0.645 | — | — | 10.370 (Supersil silica) |
| 68 | 65.561 3.448 69.483 | 11.941 | 7.544 | 4.940 | 4.405 | 0.100 | 0.666 | 0.299 | — | — | — | 0.423 | — | 0.198 | |
| 69 | 62.535 6.943 69.506 | 11.922 | 7.548 | 4.943 | 4.408 | 0.100 | 0.766 | 0.299 | — | — | — | 0.508 | — | — | |
| 70 | 71.702 | 9.632 | 5.977 | 4.980 | 4.371 | 0.200 | 1.992 | 0.299 | — | — | — | 0.848 | — | — | |
| 71 | 64.523 7.179 69.006 | 9.617 | 8.959 | 4.916 | 4.368 | — | 2.488 | — | — | — | — | 0.645 | — | — | 10.366 (fused silica fiber) |
| 72 | 62.095 6.911 69.006 62.095 6.911 | 9.617 | 8.959 | 4.916 | 4.368 | — | 2.488 | — | — | — | — | 0.645 | — | — | 2.196 (Ta) |

TABLE I-continued

Raw Porcelain Compositions, mole %

| Batch No. | Frit Fraction SiO$_2$ Solubilized | Cab-O-Sil | Al$_2$O$_3$ | B$_2$O$_3$ | K$_2$O | Na$_2$O | NaF | Li$_2$O | LaF | ZrO$_2$ | CaO | MgO | P$_2$O$_5$ | ZnO | SnO$_2$ | Filler Fraction, Weight % |
|---|---|---|---|---|---|---|---|---|---|---|---|---|---|---|---|---|
| 73 | 69.006 62.095 | 6.911 | 9.617 | 8.959 | 4.916 | 4.368 | — | 2.488 | — | — | — | — | 0.645 | — | — | 10.366 (Hydrated Alumina) |
| 74 | 69.006 62.095 | 6.911 | 9.617 | 8.959 | 4.916 | 4.368 | — | 2.488 | — | — | — | — | 0.645 | — | — | 5.649 (Ti Metal) |
| 75 | 69.006 62.095 | 6.911 | 9.617 | 8.959 | 4.916 | 4.368 | — | 2.488 | — | — | — | — | 0.645 | — | — | 9.661 (Pyrex Fiber) 9.661 F. |
| 76 | 76.006 69.282 | 7.796 | 10.728 | — | — | — | — | 4.026 | — | — | — | — | — | 4.478 | 3.800 | — |

*All SiO$_2$ from solubilized silica unless divided on next line.

Fine unfused alumina, quartz, glass fiber and plasma sprayed silica (cab-O-Sil) are encapsulated easily by a fluid sol which then is rapidly gelled.

Fine tantalum metal powder is added to one batch to effect better bonding to a metallic substrate, a tougher bonding porcelain, and through partial oxidation of the metal, a pure white optical opacification. Also, fine powders of titanium metal are added in the preparation of one batch of a tough-bonding porcelain to promote the development of an alloy-type bond to a metallic substrate, particularly to a base-metal alloy.

All porcelains are prepared for firing as small bars 19.8 mm long ×2.54 mm wide and with a thickness of 4 mm. These bars are formed in a hardened steel clamshell mold at 361 kg/cm². Form retention, color shade, gloss, bubble structure and translucency relative to tooth of the porcelain bars are determined before conducting the modulus of rupture break test by the triple point method.

Before firing, the green porcelain bars are placed on 30×7 mm strips of one mil thick platinum foil. Each strip of foil is set on a sawed piece of high temperature insulating refractory brick (k-30, Babcock and Wilcox, Augusta, Ga.). A porcelain crucible is inverted over each bar. These crucibles have heights of 4½ cm, apertures of 5 cm and bases of 2.8 cm. Then the bars are thrust into a Lindberg muffle furnace at various attained temperature settings (Lindberg Corp., Chicago, Ill.). Specimen peak temperature becomes steady in about 12 minutes.

DISCUSSION

It is observed that current commercial air and vacuum fired low-fusing porcelains used for ceramic-metal constructions when air fired by the described technique for 12 minutes mature at peak temperatures no lower than 960° C. Examination of Table II shows that about half the minus-200-mesh experimental porcelains fuse to maturity in 12 minutes at temperatures less than 960° C. Only two mature in 12 minutes at higher temperatures than the 982° C. designated by the manufacturer as the fusion temperature of Ceramco gingival porcelain.

Comparison of the form retention of experimental minus-200-mesh porcelains with commercially available porcelains indicates that at many of the higher temperatures, experimental porcelains have greater form retention at full maturity than any of the examined commercial porcelains fired to full maturity (Tables II and III).

Low fusibility without the input of excessive boric acid and alkali which increase oral solubility is particularly desirable for porcelains to be used in ceramic-metal constructions. Most of the low-fusing experimental porcelains compositionally appear to promise low solubility, and, therefore, appear particularly suitable for ceramic-metal constructions.

Several of the translucent experimental porcelain formulations when fired to full maturity have flexure strengths even in the very coarse minus-100 size equal to low-fusing commercial porcelains also fired to maturity (Table IV). It is evident that most of these gel route prepared minus-200-mesh formulations are equal in flexure strength to the low-fusing commercial porcelains, Ceramco and Will-Ceram (Table V).

The firing shrinkage of both minus-100 and minus-200-mesh porcelains are about the same as those of aesthetic non-aluminous commercial porcelains.

TABLE II

Fusibility, Form Retention and Translucency
(Experimental Porcelains, minus-200 Mesh)

| Batch No. | Fusion Temp., °C. | Time, min. | Form* Retention | Translucency Relative to Tooth |
|---|---|---|---|---|
| 69-1 | 1000 | 16 | 2–3 | greater |
| 68-1 | 990 | 12 | 1–2 | greater |
| 60-1 | 980 | 16 | 2 | same |
| 61-1 | 980 | 16 | 2–3 | same |
| 73-1 | 980 | 16 | 2 | same |
| 41-2 | 980 | 12 | 2 | same |
| 42-1 | 980 | 12 | 2–3 | greater |
| 70-1 | 960 | 12 | 2 | same |
| 6-1 | 940 | 7½ | 3 | same |
| 23-1 | 940 | 7½ | 3–4 | same |
| 54-1 | 940 | 7½ | 5 | opaque |
| 55-1 | 940 | 7½ | 5 | opaque |
| 56-1 | 940 | 7½ | 5 | opaque |
| 57-1 | 940 | 7½ | 5 | opaque |
| 63-1 | 912 | 12 | 2–3 | same |
| 75-2 | 905 | 12 | 2–3 | slightly less |
| 66-1 | 905 | 12 | 2–3 | slightly less |
| 71-1 | 900 | 12 | 2 | greater |
| 64-1 | 895 | 12 | 3 | same |
| 67-1 | 895 | 12 | 2 | same |
| 58-1 | 879 | 12 | 3 | slightly less |
| 37-2 | 878 | 12 | 2–3 | greater |
| 65-2 | 875 | 12 | 2–3 | slightly less |
| 45-3 | 869 | 12 | 2–3 | same |
| 53-1 | 900 | 8 | 4 | opaque |

*(The scale for form retention ranges from 1 to 5, with 1 best and 5 worst.)

TABLE III

Commercial Porcelains

| Sample Description | | Fusion Conditions | | Firing Shrinkage, Vol. % | Density g/cm³ | Porcelain Appearance | | | Flexure Strength, ±50 kg/cm² |
|---|---|---|---|---|---|---|---|---|---|
| Product | Lot No. | Temp., °C. | Time, min. | | | Translucency | Maturity | Deformation | |
| Will-Ceram* | Shade #81 | 964 | 12 | 32.0 | 2.44 | same | mature | 2 | 713 |
| Bioform- | #0233 | 975 | 12 | 32.2 | 2.44 | same | mature | 2 | 622 |
| Body | | 978 | 12 | 31.9 | 2.44 | same | mature | 2 | 795 |
| Incisal | E-2 #0236 | 978 | 12 | 31.5 | 2.43 | same | mature | 2 | 730 |
| Opaque | 06 #0232 | 990 | 12 | 30.3 | 2.61 | opaque | slightly under | 1–2 | 1182 |
| Biobond** | B-65 | 995 | 16 | 30.1 | 2.38 | same | mature | 2 | 623 |
| Body | #293 | 996 | 21 | 30.7 | 2.38 | same | mature | 2–3 | 571 |
| | | 1000 | 18 | 30.6 | 2.39 | same | mature | 2–3 | 629 |
| Ceramco+ | blue | 978 | 7½ | 32.9 | 2.35 | n.d. | under | n.d. | 605 |
| Modifier (air fired) | #576 | 995 | 16 | 31.6 | 2.33 | same | slightly over | 3 | 622 |
| Gingival (air fired) | 62 #946 | 975 | 7½ | 33.1 | 2.34 | n.d. | under | n.d. | 438 |
| Modifier | BF, | 980 | 31 | 32.2 | 2.34 | same | slightly | 3 | 740 |

TABLE III-continued

Commercial Porcelains

| Sample Description | | Fusion Conditions | | Firing Shrinkage, Vol. % | Density g/cm³ | Porcelain Appearance | | | Flexure Strength, ±50 kg/cm² |
|---|---|---|---|---|---|---|---|---|---|
| Product | Lot No. | Temp., °C. | Time, min. | | | Trans-lucency | Matur-ity | Defor-mation | |
| (vacuum fired) | orange #908 | 990 | 17 | 31.6 | 2.34 | same | over mature | 2–3 | 749 |
| | | 990 | 21 | 31.7 | 2.32 | same | mature | 2–3 | 729 |
| Gingival (vacuum fired) | 65, pink #1219 | 995 | 16 | 33.0 | 2.37 | same | over | 3–4 | 646 |
| Unitek++ Dentine −552 | VMK-68 #233-177 | 977 | 7½ | 32.5 | 2.43 | n.d. | under | n.d. | 825 |
| Stern Gold Bond# 1800° F. Modifier (air fired) | White #02915 | 978 | 7½ | 33.0 | 2.38 | n.d. | under | n.d. | 535 |
| Incisal (vacuum fired) | Light gray #05717 | 978 | 7½ | 37.8 | 2.37 | n.d. | under | n.d. | 315 |
| S. S. White (discon-tinued) 1700° F. (air fired) | L-55 #0035-3082 | 976 | 7½ | 35.4 | 2.47 | n.d. | mature | n.d. | 595 |
| Steele's≠ APCO (air fired) | S-66 S-32 #9913872 | 979 980 | 7½ 7½ | 36.3 34.45 | 2.31 2.345 | n.d. n.d. | under under | n.d. n.d. | 634 618.5 |
| Steele's≠ Aluminous Dentine (vacuum fired) | S-05 pink S-023 pink | 976 978 | 7½ 7½ | 40.5 40.0 | 2.36 2.34 | n.d. n.d. | under under | n.d. n.d. | 1003 738 |
| Low fusing Core (high fusing) | S-HFC-25 yellow | 982 | 7½ | 34.0 | 2.79 | n.d. | under | n.d. | 706 |
| Enamel (air fired) Low fusing | AE-2 white | 977 | 7½ | 39.5 | 2.29 | n.d. | n.d. | n.d. | 694 |

*Williams Gold Co., Buffalo, N.Y.
**Dentsply International, York, Pa.
+Johnson & Johnson, Dental Div., New Windsor, N.J.
++Vita Zahnfabrik, Sackingen, West Germany
Stern Dental Co., Mt. Vernon, N.Y.
≠Columbus Dental Manufacturing Co., Columbus, Ohio

TABLE IV

High Strength-Coarse Grained Porcelains
(Experimental Minus-100 Mesh)

| Batch No. | No. | Calcination Conditions | | Fusion Conditions | | Firing Shrinkage Vol. % | Density g/cm³ | Appearance of Porcelain | | | Flexure Strength ±50 kg/cm² |
|---|---|---|---|---|---|---|---|---|---|---|---|
| | | Temp. °C. | Time hrs | Temp. °C. | Time min | | | Trans-lucency | Mature | Round-ing* | |
| 45 | 1 | 760 | 24 1/6 | | | | | | | | |
| | 2 | 815 | 23½ | | | | | | under | | |
| | 3 | 859 | 24 | 880 | 7½ | 28.5 | 2.16 | same | | 3 | 496 |
| 49 | 1 | 725 | 20 | | | | | | | | |
| | 2 | 802 | 23½ | | | | | | under | | |
| | 3 | 860 | 24 | 940 | 7½ | 29.7 | 2.16 | same | | 1–2 | 395 |
| 53 | 1 | 875 | 2 1/6 | (1) 875 | 7½ | 28.6 | 2.13 | opaque | under | 3– | 756 |
| | | | | (2) 895 | 7½ | | | | | | |
| 54 | 1 | 875 | 2 1/6 | 890 | 7½ | 27.7 | 2.09 | opaque | under | 4 | 706 |
| | | | | 875 | 7½ | 28.7 | 2.13 | opaque | under | 3 | 722 |
| 55 | 1 | (1) 830 | 18¾ | 875 | 7½ | 29.6 | 2.15 | less | under | 3 | 539 |
| | | (2) 870 | 1 | | | | | | | | |
| 58 | 1 | 820 | 17 | (1) <600 | 7½ | 34.1 | 2.27 | same | mature | 3 | 551 |
| | | | | (2) 870 | 7½ | | | same | | | |
| 60 | 1 | 830 | 3½ | 940 | 7½ | 32.2 | 2.21 | same | under | 1–2 | 545 |
| | | | | 940 | 12 | 32.9 | 2.23 | same | under | 2 | 402 |
| 61 | 1 | 770 | 25½ | 930 | 7½ | 32.6 | 2.23 | same | under | 2 | 538 |
| | | | | 950 | 12 | 33.6 | 2.23 | same | under | 2 | 681 |
| 63 | 1 | 760 | 61 5/6 | 900 | 12 | 32.4 | 2.27 | greater | mature | 2–3 | 707 |
| | | | | 804 | 16 | 32.5 | 2.26 | greater | mature | 2–3 | 657 |
| 64 | 1 | 760 | 61 5/6 | 900 | 12 | 32.5 | 2.27 | same+ | mature | 3 | 697 |
| | | | | 904 | 16 | 29.3 | 2.21 | same+ | over | 3–4 | not broken |

TABLE IV-continued

High Strength-Coarse Grained Porcelains
(Experimental Minus-100 Mesh)

| Batch No. | No. | Calcination Conditions Temp. °C. | Time hrs | Fusion Conditions Temp. °C. | Time min | Firing Shrinkage Vol. % | Density g/cm³ | Appearance of Porcelain Trans-lucency | Mature | Round-ing* | Flexure Strength ±50 kg/cm² |
|---|---|---|---|---|---|---|---|---|---|---|---|
| 65 | 1 | 775 | 3½ | 900 | 12 | 31.8 | 2.25 | greater | mature | 2-3 | 567 |
|    | 2 | 765 | 26 | | | | | | | | |
| 66 | 1 | 775 | 14 1/6 | 900 | 12 | 30.7 | 2.20 | same | mature | 2-3 | 557 |
|    |   |     |        | 904 | 16 | 30.0 | 2.17 | greater | mature | 2-3 | 416 |
| 67 | 1 | 770 | 22 5/6 | 900 | 12 | 31.8 | 2.22 | same+ | mature | 2-3 | 460 |
|    |   |     |        | 904 | 16 | 30.0 | 2.20 | same+ | mature | 2-3 | 423 |
| 68 | 1 | 865 | 18½ | 965 | 12 | 32.8 | 2.27 | greater | under | 2 | 638 |
|    |   |     |     | 964 | 16 | 33.4 | 2.28 | same | under | 2 | 526 |
| 69 | 1 | 825 | 40 5/6 | 965 | 12 | 32.8 | 2.24 | greater+ | mature | 1 | 563 |
|    |   |     |        | 965 | 16 | 32.5 | 2.24 | greater | mature | 2 | 524 |
| 70 | 1 | 760 | 61 5/6 | 965 | 12 | 28.5 | 2.18 | greater+ | mature | 3- | 519 |
|    |   |     |        | 965 | 16 | 28.0 | 2.17 | same+ | mature | 2-3 | 563 |
| 71 | 1 | 775 | 3½ | 900 | 12 | 33.7 | 2.21 | greater+ | mature | 2-3 | 562 |
|    |   |     |    | 904 | 16 | 33.6 | 2.20 | same+ | mature | 2-3 | 730 |
| 72 | 1 | 770 | 14 5/6 | 900 | 12 | 33.7 | 2.29 | greater+ | mature | 3 | 542 |
|    |   |     |        | 904 | 16 | 33.1 | 2.27 | greater+ | mature | 3 | 533 |
| 73 | 1 | 825 | 40 5/6 | (1) 900 | 12 | | | | | | |
|    |   |     |        | (2) 925 | 12 | 34.2 | 2.25 | same+ | mature | 2 | 929 |
|    |   |     |        | (3) 965 | 12 | | | | | | |
|    |   |     |        | 964 | 16 | 33.3 | 2.24 | greater | mature | 2 | 617 |
| 75 | 1 | (1) 860 | 22 5/6 | | | | | | | | |
|    |   | (2) 890 | ⅔ | 898 | 12 | 31.4 | 2.29 | same | mature | 2* | 701 |
|    | 2 | 870 | 19½ | 900 | 12 | 32.1 | 2.28 | same | mature | 2* | 779 |

+Specimen appeared grainy
*Rounding measured on scale 1-6 with one being no rounding.

TABLE V

High-Strength Intermediate-Grained Porcelains
(Experimental Minus-200 Mesh)

| Batch No. | No | Calcination Conditioning Temp., °C. | Time, hrs. | Position Conditioning Temp., °C. | Time min. | Firing Shrinkage, Vol. % | Density, g/cm³ | Porcelain Appearance Trans-lucency | Matur-ity | Deform-ation | Flexure Strength |
|---|---|---|---|---|---|---|---|---|---|---|---|
| 27 | 1 | 650 | 21 5/6 | | | | | | | | |
|    | 2 | 725 | 17½ | 940 | 7½ | 32.0 | 2.13 | same | mature | 3-4 | 580 |
|    |   |     |     | 950 | 7¾ | 31.5 | 2.13 | same | mature | 3-4 | 630* |
| 28b | 1 | 650 | 23 1/6 | | | | | | | | |
|     | 2 | 770 | 21 1/6 | 940 | 7½ | 33.7 | 2.22 | same | under | 2 | 644 |
| 31a | 1 | 710 | 23 | 1940 | 7½ | | | | | | |
|     |   |     |    | 3955 | 10 | 38.1 | 2.22 | greater | under | 1-2 | 469 |
| 36b | 1 | 650 | 22 | | | | | | | | |
|     | 2 | 772 | 22⅝ | 935 | 7½ | 32.7 | 2.19 | same | under | | 646 |
| 37 | 1 | 650 | 23 1/6 | 935 | 7½ | 36.0 | 2.27 | greater | over | 5 | 604 |
|    | 2 | 770 | 21 1/6 | 878 | 12 | 34.3 | 2.24 | greater | mature | 2-3 | 774 |
|    |   |     |        | 902 | 12 | 35.5 | 2.25 | greater | over | 3 | 664 |
|    |   |     |        | 910 | 12 | 34.6 | 2.25 | greater | over | 3 | 807 |
| 45 | 1 | 760 | 24 1/6 | | | | | | | | |
|    | 2 | 815 | 23½ | | | | | | | | |
|    | 3 | 859 | 24 | 855 | 12 | 32.5 | 2.20 | less | under | 1 | 656* |
|    |   |     |    | 869 | 12 | 32.2 | 2.18 | same | mature | 2-3 | 645 |
|    |   |     |    | 868 | 16 | 32.3 | 2.185 | same | mature | 3 | 609* |
|    |   |     |    | 860 | 20 | 32.8 | 2.20 | same | slightly under | 2 | 687* |
| 47 | 1 | 802 | 23½ | | | | | | | | |
|    | 2 | 860 | 24 | 930 | 7½ | 32.1 | 2.14 | n.d. | n.d. | n.d. | 422 |
| 48 | 1 | 802 | 23½ | | | | | | | | |
|    | 2 | 860 | 24 | 930 | 7½ | 34.4 | 2.10 | n.d. | n.d. | n.d. | 447 |
| 49 | 1 | 725 | 20 | | | | | | | | |
|    | 2 | 802 | 23½ | 945 | 7½ | 37.1 | 2.16 | n.d. | n.d. | n.d. | 533 |
|    | 3 | 860 | 24 | 980 | 26 | 37.2 | 2.21 | same | slightly under | 1-2 | 708 |
|    |   |     | 24 | 980 | 26 | 35.5 | 2.22 | same | slightly under | 2 | 894* |
| 50 | 1 | 725 | 21⅝ | | | | | | | | |
|    | 2 | 805 | 23½ | 950 | 7½ | 36.6 | 2.17 | n.d. | n.d. | n.d. | 541 |
| 52 | 1 | 725 | 21⅝ | | | | | | | | |
|    | 2 | 805 | 23½ | 940 | 7½ | 34.3 | 2.17 | n.d. | n.d. | n.d. | 498 |
| 58 | 1 | 820 | 17 | 879 | 12 | 36.0 | 2.25 | slightly less | mature | 3 | 772 |
|    |   |     |    | 898 | 12 | 35.0 | 2.25 | slightly less | mature | 3 | 627* |
|    |   |     |    | 900 | 12 | 35.15 | 2.255 | slightly less | mature | 3 | 618 |

TABLE V-continued

High-Strength Intermediate-Grained Porcelains
(Experimental Minus-200 Mesh)

| Batch No. | Calcination Conditioning No | Calcination Conditioning Temp., °C. | Calcination Conditioning Time, hrs. | Position Conditioning Temp., °C. | Position Conditioning Time min. | Firing Shrinkage, Vol. % | Density, g/cm³ | Porcelain Appearance Translucency | Porcelain Appearance Maturity | Porcelain Appearance Deformation | Flexure Strength |
|---|---|---|---|---|---|---|---|---|---|---|---|
| 60 | 1 | 830 | 3¼ | 975 | 12 | 36.6 | 2.23 | same | slightly under | 2 | 841 |
|   |   |   |   | 980 | 16 | 36.0 | 2.23 | same | mature | 2 | 736 |
|   |   |   |   | 980 | 16 | 35.7 | 2.23 | same | mature | 2 | 647* |
|   |   |   |   | 980 | 28 | 35.4 | 2.22 | same | mature | 2 | 766 |
| 61 | 1 | 770 | 25½ | 940 | 7½ | 36.3 | 2.22 | slightly greater | slightly under | 2 | 657 |
|   |   |   |   | 980 | 12 | 35.4 | 2.22 | same | mature | 2 | 519 |
|   |   |   |   | 980 | 16 | 35.0 | 2.22 | same | mature | 2-3 | 710 |
|   |   |   |   | 980 | 16 | 35.0 | 2.23 | same | mature | 2 | 747* |
| 63 | 1 | 760 | 61 5/6 | 912 | 12 | 35.1 | 2.26 | same | mature | 2-3 | 705 |
|   |   |   |   | 912 | 12 | 34.8 | 2.25 | greater | mature | 2-3 | 683* |
| 64 | 1 | 760 | 61 5/6 | 895 | 12 | 34.7 | 2.25 | same | mature | 3 | 674 |
|   |   |   |   | 895 | 14 | 34.4 | 2.24 | same | mature | 3 | 620 |
|   |   |   |   | 912 | 12 | 34.6 | 2.23 | same | over | 4 | 709* |
| 65 | 1 | 775 | 3½ |  |  |  |  |  |  |  |  |
|   | 2 | 765 | 26 | 875 | 12 | 34.3 | 2.235 | slightly less | mature | 2-3 | 660 |
|   |   |   |   | 900 | 12 | 34.4 | 2.225 | slightly less | mature | 2-3 | 660 |
|   |   |   |   | 900 | 12 | 34.3 | 2.22 | slightly less | mature | 2-3 | 599* |
|   |   |   |   | 900 | 21 | 34.0 | 2.22 | slightly less | over | 4 | 683* |
| 66 | 1 | 775 | 146 | 905 | 12 | 31.75 | 2.19 | slightly less | mature | 2-3 | 613 |
|   |   |   |   | 905 | 14 | 31.3 | 2.18 | slightly less | mature | 2-3 | 636 |
|   |   |   |   | 905 | 32 | 30.3 | 2.15 | less | over | 4-5 | 578* |
| 67 | 1 | 770 | 22 5/6 | 895 | 12 | 34.5 | 2.23 | same | mature | 2 | 494 |
|   |   |   |   | 898 | 12 | 34.0 | 2.22 | same | mature | 2 | 595* |
|   |   |   |   | 900 | 12 | 33.6 | 2.22 | same | mature | 2 | 537 |
|   |   |   |   | 902 | 12 | 34.2 | 2.215 | same | mature | 2 | 604 |
| 68 | 1 | 865 | 18½ | 978 | 16 | 35.4 | 2.26 | greater | slightly under | 1-2 | 711 |
|   |   |   |   | 980 | 16 | 35.0 | 2.27 | greater | slightly under | 1-2 | 720 |
|   |   |   |   | 985 | 16 | 34.9 | 2.26 | greater | slightly under | 1-2 | 740 |
|   |   |   |   | 990 | 16 | 35.65 | 2.265 | greater | mature | 1-2 | 705 |
| 69 | 1 | 825 | 40 5/6 | 978 | 16 | 35.2 | 2.23 | greater | slightly under | 2 | 711 |
|   |   | 816 |   | 1000 | 16 | 35.2 | 2.23 | greater | mature | 2-3 | 816 |
|   |   |   |   | 990 | 31 | 35.0 | 2.24 | greater | slightly over | 3 | 735* |
| 70 | 1 | 760 | 61 5/6 | 958 | 12 | 31.2 | 2.21 | same | mature | 2 | 753 |
|   |   |   |   | 960 | 12 | 31.1 | 2.21 | same | mature | 2 | 652 |
|   |   |   |   | 972 | 12 | 30.6 | 2.20 | same | mature | 3 | 789 |
|   |   |   |   | 985 | 12 | 30.4 | 2.19 | slightly less | slightly over | 3-4 | 647 |
|   |   |   |   | 985 | 12 | 30.7 | 2.19 | slightly less | mature | 3 | 641* |
| 71 | 1 |   |   | 900 | 12 | 36.1 | 2.22 | greater | mature | 2 | 721 |
|   |   |   |   | 905 | 12 | 34.55 | 2.215 | greater | mature | 2 | 708 |
|   |   |   |   | 905 | 13 | 35.8 | 2.21 | greater | mature | 2 | 658 |
|   |   |   |   | 908 | 12 | 35.5 | 2.22 | greater | mature | 2 | 608* |
|   |   |   |   | 910 | 12 | 36.6 | 2.21 | greater | mature | 2 | 551 |
| 72 | 1 | 770 | 14 5/6 | 897 | 12 | 34.7 | 2.28 | same | mature | 3 | 778 |
|   |   |   |   | 898 | 12½ | 34.6 | 2.26 | same | mature | 2-3 | 699* |
|   |   |   |   | 903 | 12 | 34.0 | 2.27 | same | mature | 2-3 | 694 |
|   |   |   |   | 905 | 12 | 34.85 | 2.27 | same | mature | 2-3 | 721.5 |
|   |   |   |   | 908 | 12 | 34.8 | 2.26 | same | mature | 3 | 847 |
| 73 | 1 | 825 | 40 5/6 | 980 | <16 | 34.75 | 2.24 | same | mature | 2 | 790 |
|   |   |   |   | 988 | 16 | 34.8 | 2.23 | same | mature | 2 | 814 |
|   |   |   |   | 990 | 16 | 34.7 | 2.23 | same | mature | 2 | 783 |
|   |   |   |   | 990 | 16 | 35.3 | 2.23 | same | mature | 2 | 656* |
| 75 | 1 | 860 | 22 |  |  |  |  |  |  |  |  |
|   |   | 880 | ⅞ |  |  |  |  |  |  |  |  |
|   | 2 | 870 | 19½ | 905 | 12 | 33.3 | 2.24 | slightly less | mature | 2-3 | 793 |
|   |   |   |   | 901 | 12 | 33.3 | 2.24 | slightly less | mature | 2-3 | 582* |
|   |   |   |   | 905 | 16 | 33.1 | 2.22 | slightly | mature | 3 | 805 |

TABLE V-continued

High-Strength Intermediate-Grained Porcelains
(Experimental Minus-200 Mesh)

| Batch No. | Calcination Conditioning No. | Temp., °C. | Time, hrs. | Position Conditioning Temp., °C. | Time min. | Firing Shrinkage, Vol. % | Density, g/cm³ | Trans-lucency | Matur-ity | Deform-ation | Flexure Strength |
|---|---|---|---|---|---|---|---|---|---|---|---|
| | | | | | | | | less | | | |

*heat treated 24 hr. 600–700° C.

Fine grained porcelains prepared from gel route made frits by prolonged pebble milling and firing to maturity commonly exceed in strength the strongest commercial low-fusing porcelains. Aesthetic porcelains with good form retention are formulated which fuse at temperatures lower than 940° C., and when rapidly fired in less than $7\frac{1}{2}$ minutes to maturity have flexure strengths in excess of 1,021 kg/cm²(Table VI). One of the strongest commercial low-fusing porcelains is Unitek with a flexure strength of 825 kg/cm², and it is known that the classical air-firing jacket-crown porcelain Apco (Columbus Dental Manufacturing Co.) does not exceed 950 kg/cm² in flexure strength. It should be noted from the Tables that heat treatment of gel route prepared porcelains for 24 hours between 600° and 700° C. does not improve strength.

The densities of gel route prepared porcelain frits are somewhat lower than those of commercial porcelain frits (Table VII). These lower densities partly account for the lower apparent densities of porcelain bodies fabricated from these frits.

TABLE VII

PORCELAIN FRIT DENSITIES
(Low Fusing)

| Porcelain Type | Description Sample Designation | Frit Density, ±0.01 g/cm³ |
|---|---|---|
| Ceramco Modifier (vacuum fired) | orange, Lot #908 | 2.45 |
| Will Ceram Body (vacuum fired) | #81, Lot #0233 | 2.52 |
| Unitek Dentine (vacuum fired) | VMK-68 | 2.52 |
| Stern Gold Bond Incisal | Light Gray, Lot #05717 | 2.48 |
| Experimental (Batch No.) | 100–140 mesh | 2.41 |
| 41-2 | minus 200 mesh, dry milled | 2.49 |
| | minus 200 mesh, wet milled | 2.50 |
| 60-1 | 100–140 mesh | 2.39 |
| | minus 200 mesh, wet milled | 2.43 |
| 61-1 | 100–140 mesh | 2.39 |
| 65-2 | minus-200 mesh, wet milled | 2.42 |
| 67-1 | minus-200, wet milled | 2.39 |
| 71-1 | minus-200, wet milled | 2.39 |
| 75-2 | 100–140 mesh | 2.39 |

TABLE VI

High-Strength Fine-Grained Porcelains
(Experimental)

| Batch No.* | Calcination Conditions No. | Temp. °C. | Time, hrs. | Sizing and Blending | Fusion Conditions Temp., °C.** | Time, min. | Firing Shrinkage, Vol. % | Density ± 0.01 g/cm³ ≠ | Flexure Strength, ± 50 Kg/cm² |
|---|---|---|---|---|---|---|---|---|---|
| 6 | 1 | 960 | peaked | wet milled (24 hr.) | 930 | 7½ | 41.4 | 2.28 | 998 |
| | | | | | 930 heat 770° C. | 7½ treated 22 hrs. | 41.3 | 2.27 | 933 |
| 23 | 1 | 770 | 21 1/6 | wet milled (24 hr.) | 940 | 7½ | 42.2 | 2.26 | 1035 |
| 23 | 1 | 770 | 21 1/6 | wet milled (24 hr.) 75% | 930 | 7½ | 40.8 | 2.26 | 869 |
| 24 | 1 | 720 | peaked | dry milled (24 hr.) 25% | | | | | |
| 23 | 1 | 770 | 21 1/6 | wet milled (24 hr.) 50% | 928 | 7½ | 41.6 | 2.25 | 941 |
| 24 | 1 | 720 | peaked | dry milled (24 hr.) 50% | | | | | |
| 23 | 1 | 770 | 21 1/6 | wet milled (24 hr.) 25% | 930 | 7½ | 33.3 | 2.20 | 680 |
| 24 | 1 | 720 | peaked | dry milled (24 hr.) 75% | | | | | |
| 23 | 1 | 770 | 21 1/6 | wet milled (24 hr.) | | | | | |
| | 2 | 800 | 16 | 12.5% minus-100-mesh 12.5% | 925 | 7½ | 35.2 | 2.26 | 976 |
| 14 | 1 | 810 | 15¼ | dry milled (30°) 75% | | | | | |
| 6 | 1 | 960 | peaked | wet milled (24 hr.) 25% | 925 | 7½ | 36.4 | 2.26 | 1021 |
| 14 | 1 | 810 | 15¼ | dry milled (30°) 75% | | | | | |
| 5 | 1 | 620 | 17 | wet milled (24 hr.) 25% | 925 | 7½ | 38.9 | 2.23 | 914 |
| 14 | 1 | 810 | 15¼ | dry milled (30°) | | | | | |

*Porcelains are mature with translucencies nearly the same as tooth.
**Peak temperatures attained by specimens.
≠Apparent density of fired porcelain bars.

TABLE VII-continued

PORCELAIN FRIT DENSITIES (Low Fusing)

| Porcelain Type | Description Sample Designation | Frit Density, ±0.01 g/cm³ |
|---|---|---|
| | minus-200, wet milled | 2.47 |

EXAMPLE 2

Method

Frits containing (exclusive of filler) 69.0–72.3 mole percent silicon dioxide, 4.9–11.9 mole percent aluminum oxide, 6.0–9.0 mole percent boric oxide, 4.9–5.2 percent potassium oxide, 4.4–4.6 percent sodium oxide, and varying amounts (less than 1.5 percent total) of zirconium oxide, calcium oxide, magnesium oxide, phosphorus pentoxide and zinc oxide are prepared. See Table VIII. Minus-200-mesh porcelains and batch #24 contain 0.4–2.5 percent lithium oxide except for batch #45, which contains 25.0 percent and no potassium oxide and sodium oxide. Batches #'s 63 and 68–70 contain 0.1–0.30 percent of either or both lithium fluoride and sodium fluoride. Nitric acid, acetic acid, and methanol are added to peptize the sol system. To prepare porcelain composites, 10.4 weight percent of fine particles of quartz (#67), potassium-feldspar (#66), pyrex glass (#64), fused silica fiber (#71) and unfused alumina (#73) are added to the sol. Fine tantalum (#72, Ta, 2.2 percent) and titanium powders are added to make opaquing porcelains which form alloy bonds with metal bridgeworks.

Each dried gel is precalcined at 500° C. for one hour to remove nitrogen oxides, ground, and then calcined to temperatures as high as 870° C. and then either pebble milled or stage-ground through 200-mesh.

TABLE VIII

Experimental Porcelains

| Batch No. | Firing Temp., °C. | Firing Shrinkage ±1 Vol. % | Density ±0.01 g/cm³ | Flexure Strength ±50 kg/cm² |
|---|---|---|---|---|
| I. Pebble-milled (7½ min. fire) | | | | |
| 6 | 930 | 41.4 | 2.28 | 998 |
| 6-14 | 925 | 36.4 | 2.26 | 1021 |
| 5-14 | 925 | 38.9 | 2.23 | 914 |
| 23-24 | 928 | 41.6 | 2.25 | 941 |
| 23-14 | 925 | 35.2 | 2.26 | 976 |
| 23 | 940 | 42.2 | 2.26 | 1035 |
| II. Minus-200-mesh (12 min. fire, [1]min.16) | | | | |
| 37 | 878 | 34.3 | 2.24 | 774 |
| 45 | 869 | 32.2 | 2.18 | 645 |
| 60 | 975 | 36.6 | 2.23 | 841 |
| 63 | 912 | 35.1 | 2.26 | 705 |
| 64 | 895 | 34.7 | 2.25 | 674 |
| 65 | 875 | 34.3 | 2.235 | 660 |
| 66 | 905 | 31.75 | 2.19 | 613 |
| 67 | 902 | 34.2 | 2.215 | 604 |
| 68(1) | 985 | 34.9 | 2.26 | 740 |
| 69(1) | 1000 | 35.2 | 2.23 | 816 |
| 70 | 958 | 31.2 | 2.21 | 753 |
| 71 | 900 | 36.1 | 2.22 | 721 |
| 72 | 908 | 34.8 | 2.26 | 847 |
| 73(1) | 988 | 34.8 | 2.25 | 814 |

DISCUSSION

Porcelains with superior form retention, good translucency, short firing times and very low fusion temperatures are obtained. Most of these frits fire to maturity at peak temperatures lower than 960° C. in a 12 minute air fire. Even without optimization of particle size distribution, firing shrinkages generally are within the range of low fusing commercial porcelains. Frit densities of minus-200-mesh porcelains vary from 2.39–2.50, averaging slightly lower than commercial porcelains. Triple point flexure strengths of all minus-200-mesh experimental porcelains are within the range of five low-fusing commercial porcelains similarly fired to maturity. Pebble-milled porcelains exceed in flexure strength any of the commercial porcelains, including the air fired Apco with 850 kg/cm². Only one of the five commercial metal-ceramic porcelains achieves maturity in 7½ minute air fires below 960° C., whereas all the pebblemilled experimental porcelains do.

EXAMPLE 3 (COMPARATIVE EXAMPLE)

All porcelain frits must be specifically formulated as to their particular intended function as body, modifying, opaquing and bonding porcelains or as glazes. A common requirement is that porcelain have a coefficient of thermal expansion somewhat less than the substrate so that it will not craze or peel. Porcelains must be formulated to be fired over dental gold, base-metal and palladium-silveralloys whose collective coefficients of thermal expansion commonly range from 13 to $15 \times 10^{-6}/°C$.

Some porcelains are formulated to fire on alumina preforms, whose average coefficients in the normal firing range are between 7 and $8 \times 10^{-6}/°C$., or over aluminous porcelain cores with a similar coefficient of expansion. When total nonaluminous porcelain restorations are made, porcelain construction commonly is made over platinum foil, with an average coefficient of thermal expansion of approximately $9 \times 10^{-6}/°C$. Occasionally, punched platinum-iridium foils are used to build up porcelain constructions which have thermal expansions ranging between 7.5 and $9 \times 10^{-6}/°C$.

The experimental porcelain compositions of this example are formulated to fire into a frit on relatively low thermal expansion substrates with coefficients between 7 and $9 \times 10^{-6}/°C$.

METHOD

Sols are prepared according to the preferred means described above, resulting in compositions as shown in Table IX. The gel compositions are allowed to set under constant stirring over a hot plate at 100–200° C. to the rigidity of a medium to hard putty. They are then dessicated in a forced-air drying oven for 20 to 30 hours at 90° to 100° C., and then for 20 to 30 hours at 190° to 200° C. In all runs, specimens are raised to the 90° to 100° C. temperature from room temperature and from this temperature to 190° to 200° C. within one hour. Defuming for one hour at each of 500, 600 and 700° C. is then carried out, followed by stage-grinding in a mullite mortar through 40-mesh.

Calcination involves step-wise heating of precalcined frit to 960° C. The minus-40-mesh precalcined frit is placed in a suitably sized porcelain crucible and heated in a muffle furnace at successive 25° C. intervals for one hour from an initial temperature of 725° C. Calcination is continued until a dense high-biscuit-type gloss is obtained. If the fritted mass becomes bloated, it is ground through 40 mesh and recalcined. Up to four calcinations are commonly required and in some instances up to ten are required. Most of the compositions are stage-ground through 40-mesh before calcination, and precalcination defuming temperatures do not exceed 700° C. The frit compositions of the low alkali porcelains vary in mole percent as follows: 69–73 percent silicon dioxide, 7.5–9.6 aluminum oxide, 5.0–9.6 boric oxide, 3.0–6.3 percent potassium oxide, 2.8–4.5 percent sodium oxide, and 0.5–5.0 lithium oxide. In some instances, very small amounts of zirconium, magnesium, phosphorus, zinc and tin oxide, tantalum, titanium, barium and strontium oxides are added. See Table IX.

Also, form retention is characterized on cylindrical specimens prepared from raw porcelain frit by pelletization under an applied stress of 454 kg/cm$^2$ which are fired to maturity in the standard 12 minute fire. The green pellets are prepared in a hardened steel die with a diameter of 12.70 mm to heights varying between 6 and 7 mm. These cylindrical specimens fired to maturity are also used for the solubility tests.

TABLE IX

Composition of Experimental Porcelains (Minus-140 mesh)

| Sample Designation | Mole Percent Oxide | | | | | | | | | | | Specimen Maturation Temperature, °C. |
|---|---|---|---|---|---|---|---|---|---|---|---|---|
| | $SiO_2$ | $Al_2O_3$ | $B_2O_3$ | $K_2O$ | $Na_2O$ | $Li_2O$ | $ZrO_2$ | $CaO$ | $MgO$ | $P_2O_5$ | $ZnO$ | $SnO_2$ | |
| A. Low-alkali content | | | | | | | | | | | | | |
| 94-1 | 71.0 | 7.6 | 5.0 | 4.0 | 4.0 | 1.0 | 0.5 | 0.4 | 0.4 | 2.1 | 4.0 | — | 1006 |
| 88-1b | 71.0 | 9.5 | 7.0 | 5.4 | 4.4 | | | | | 0.7 | 1.0 | 1.0 | 1009 |
| 90-1b | 71.0 | 9.5 | 7.0 | 4.0 | 4.4 | 1.0 | | 0.4 | | 0.7 | 1.0 | 1.0 | 1014 |
| 91-1b | 71.0 | 9.5 | 7.0 | 4.0 | 4.0 | 1.0 | | 0.4 | 0.4 | 0.7 | 1.0 | 1.0 | 1036 |
| 93-1b | 71.0 | 8.6 | 6.0 | 4.0 | 4.0 | 1.0 | 0.5 | 0.4 | 0.4 | 1.1 | 2.0 | 1.0 | 1043 |
| 95-1b | 70.0 | 7.6 | 5.0 | 4.0 | 4.0 | 2.0 | | 0.4 | 0.4 | 2.6 | 4.0 | | 1052 |
| 92-1b | 71.0 | 9.5 | 6.5 | 4.0 | 4.0 | 1.0 | 0.5 | 0.4 | 0.4 | 0.7 | 1.0 | 1.0 | 1073 |
| 96-1b | 70.0 | 7.6 | 5.0 | 3.0 | 4.0 | 2.0 | | | | 2.6 | 4.0 | 1.8 | 1084 |
| 81-1b | 74.6 | 12.35 | 5.45 | 3.0 | 4.5 | — | — | 0.1 | — | — | — | — | <<1126 |
| B. High-alkali content | | | | | | | | | | | | | |
| 147 | 63.0 | 5.5 | 3.0 | 10.0 | 18.0 | 0.5 | — | — | — | — | — | — | (bloated frit) |
| 148 | 63.95 | 7.55 | 5.5 | 8.0 | 14.5 | 0.5 | — | — | — | — | — | — | " |
| 149 | 66.0 | 5.5 | 5.5 | 8.0 | 14.5 | 0.5 | — | — | — | — | — | — | " |
| 150 | 68.05 | 7.45 | 5.5 | 6.0 | 12.5 | 0.5 | — | — | — | — | — | — | " |
| 154 | 74.9 | 9.0 | 6.4 | 5.1 | 4.6 | — | — | — | — | — | — | — | n.d.* |
| 155 | 68.4 | 12.6 | 4.6 | 8.7 | 5.2 | — | — | — | — | — | 0.5 | — | (frozen frit) |
| 156 | 73.5 | 9.5 | 1.5 | 7.2 | 6.6 | — | — | 1.7 | — | — | — | — | 987 |
| 157 | 67.6 | 12.5 | 4.5 | 8.6 | 5.8 | 0.5 | — | — | — | — | 0.5 | — | (frozen frit) |
| 158 | 63.0 | 4.5 | 3.0 | 11.0 | 18.0 | 0.5 | — | — | — | — | — | — | (used as filler for #159) |
| 159 | 69.5 | 9.6 | 9.6 | 4.9 | 4.0 | 2.4 | — | — | — | — | — | — | 872 |
| 160 | 70.0 | 8.9 | 5.65 | 8.1 | 5.85 | 0.0 | — | 1.2 | — | — | — | 0.3 | 916 |
| 161 | 70.0 | 8.9 | 5.65 | 4.1 | 5.85 | 4.0 | — | 1.2 | — | — | — | 0.3 | 871 |
| 162 | 70.0 | 8.9 | 5.65 | 8.1 | 3.85 | 2.0 | — | 1.2 | — | — | — | 0.3 | 920 |

*Not determined

Small cylinders of raw porcelain (dia. 5.5 mm; ht., 13–16 mm) are pelletized under an applied pressure of 1,200 kg/cm$^2$. These pelletized porcelains are fired to maturity in a 12 minute air fire. The ends of these cylinders are ground parallel to a length of 10 mm. Then each specimen is inserted into a Theta vertical dilatometer (Theta Industries, Port Washington, N.Y.). Before making thermal dimensional determinations, thin circular plates of electronic substrate alumina (dia. 5.2 mm; thickness 0.320–0.325 mm) are mounted at each end of the porcelain specimen.

Categories of small bar deformation on firing are set up from one to six with the lowest value being the best. These bars are prepared by pelletizing raw porcelain at 1,138 kg/cm$^2$ in a hardened steel die to the dimensions 19.8 mm long by 2.565 mm wide and to thicknesses varying between 3.8 and 4.6 mm.

After these small bars are fired, their volumes are determined hydrostatically. The change in volume from that of the green bar prepared from raw porcelain is used to determine the firing shrinkage. Thus both commercial and experimental frit test specimens are constructed identically. For flexure strength measurements, these bars are machined and polished by optical preparation procedures to 2.0 mm thick by 1.3 mm wide and tested under a triple-point load with a span of 11.943 mm.

A cylindrical ratio is calculated from measurements of the above fired pellets. Volume of the pellets after firing is determined hydrostatically, and from the average maximum diameter (five measurements) and average height (four measurements), a calculated volume is determined. The ratio of the actual volume to the calculated volume is determined for the commercial and gel route prepared products. The greater this ratio, the greater is the form retention of mature, but not overfired, porcelains.

DISCUSSION

Gel route prepared frit densities have been observed to vary from 2.39 to 2.50 g/cm$^3$. This is lower than the commercial metal-ceramic body porcelains which commonly vary from 2.46–2.52 g/cm$^3$. See Table VII. Inventive porcelains fired from pebble-milled gel route prepared frit exhibit triple-point flexure strengths of 976 to 1035 kg/cm$^2$ (Table X). Maturation of these porcelains occurs in 7½ minutes with specimen peak temperatures from 920 to 940° C.

The triple-point flexure strengths of small optically ground bars of porcelain with tooth translucency prepared from minus-140-mesh (U.S. Standard Sieves) low-alkali gel route derived frits vary from about 630 to 1000 kg/cm$^2$ (Table XI). This range in strength is approximately that of common commercial non-aluminous porcelains, i.e., from 650 to 950 kg/cm$^2$ (Table XII).

TABLE X

High-Strength Fine-Grained Porcelains (Experimental)

| Batch No.* | Calcination Conditions No. | Calcination Conditions Temp. °C. | Calcination Conditions Time hrs. | Sizing and Blending | Fusion Conditions Temp. °C.** | Fusion Conditions Time, min. | Firing Shrinkage, Vol. % | Density ±0.01 g/cm³ ≠ | Flexure Strength = 50 Kg/cm² |
|---|---|---|---|---|---|---|---|---|---|
| 6 | 1 | 960 | peaked | wet milled (24 hr.) | 930 | 7½ | 41.4 | 2.28 | 998 |
|   |   |     |        |                     | 930 heat treated 770° C. | 7½ 22 hrs. | 41.3 | 2.27 | 933 |
| 23 | 1 | 770 | 21 1/6 | wet milled (24 hr.) | 940 | 7½ | 42.2 | 2.26 | 1035 |
|    |   |     |        | 75% |   |   |   |   |   |
| 23 | 1 | 770 | 21 1/6 | wet milled (24 hr.) 25% | 930 | 7½ | 40.8 | 2.26 | 869 |
| 24 | 1 | 720 | peaked | dry milled (24 hr.) 50% |   |   |   |   |   |
| 23 | 1 | 770 | 21 1/6 | wet milled (24 hr.) 50% 50% | 928 | 7½ | 41.6 | 2.25 | 941 |
| 24 | 1 | 720 | peaked | dry milled (24 hr.) 25% |   |   |   |   |   |
| 23 | 1 | 770 | 21 1/6 | wet milled (24 hr.) 75% | 930 | 7½ | 33.3 | 2.20 | 680 |
| 24 | 1 | 720 | peaked | dry milled (24 hr.) 75% |   |   |   |   |   |
| 23 | 1 | 770 | 21 1/6 | wet milled (24 hr.) |   |   |   |   |   |
|    | 2 | 800 | 16 | 12.5% minus-100-mesh 12.5% | 925 | 7½ | 35.2 | 2.26 | 976 |
| 14 | 1 | 810 | 15¼ | dry milled (30°) 75% |   |   |   |   |   |
| 6 | 1 | 960 | peaked | wet milled (24 hr.) 25% | 925 | 7½ | 36.4 | 2.26 | 1021 |
| 14 | 1 | 810 | 15¼ | dry milled (30°) 75% |   |   |   |   |   |
| 5 | 1 | 620 | 17 | wet milled (24 hr.) 25% | 925 | 7½ | 38.9 | 2.23 | 914 |
| 14 | 1 | 810 | 15¼ | dry milled (30°) |   |   |   |   |   |

*Porcelains are mature with translucencies nearly the same as tooth.
**Peak temperatures attained by specimens.
≠Apparent density of fired porcelain bars.

TABLE XI

Flexure Strength of Experimental Porcelains* (Low alkali content)

A. Porcelains with Good Translucency

| Designation | Specimen Maturation Temp., °C. (12 min fire) | Apparent Density ±0.01 g/cm³ | Firing Shrinkage Vol. % | Flexure Strength ±50 kg/cm² |
|---|---|---|---|---|
| 80-3 | 940 | 2.26 | 31.7 | 996 |
| 79-2 | 930 | 2.28 | 33.2 | 913 |
| 85-2 | 883 | 2.26 | 32.3 | 906 |
| 91-1b | 1036 | 2.32 | 34.7 | 834 |
| 82-2 | 830 | 2.265 | 34.3 | 787 |
| 89-1b | 987 | 2.31 | 34.9 | 768 |
| 86-2 | 883 | 2.28 | 33.7 | 726 |
| 87-1 | 935 | 2.24 | 35.3 | 694 |
| 84-2 | 903 | 2.24 | 31.7 | 689 |
| 88-1 | 1009 | 2.31 | 33.7 | 687 |
| 78-1 | 962 | 2.23 | 34.4 | 627 |

B. Porcelains with Poor Translucency

| Designation | Specimen Maturation Temp., °C. (12 min fire) | Apparent Density to .01 g/cm³ | Firing Shrinkage Vol. % | Flexure Strength ±50 kg/cm² |
|---|---|---|---|---|
| 93-1b | 1043 | 2.34 | 33.3 | 845 |
| 96-1b | 1084 | 2.34 | 31.6 | 724 |
| 94-1 | 1006 | 2.29 | 31.8 | 670 |
| 95-1 | 7052 | 2.30 | 31.6 | 668 |
| 92-1 | 1073 | 2.34 | 34.3 | n.d. |

*See Footnote 1 on Table XII
**Translucencies equal to or better than tooth

TABLE XII

Flexure Strength of Commercial Porcelains[1]

| Designation[5] | Specimen Maturation Temp., °C. (12 min. fire) | Apparent Density to .01 g/m³ | Firing Shrinkage Vol. % | Flexure Strength ±50 kg/cm² |
|---|---|---|---|---|
| Neydium V[2], Body B-1 (vacuum fired) | 1002 | 2.42 | 37.7 | 943 |
| Will Ceram, Body B-81 (vacuum fired) | 975 | 2.44 | 32.7 | 928 |
| Apco[3], S-32 (air-fired) | 1025 | 2.33 | 35.8 | 817 |
| Ceramco Gingival B-81 (vacuum-fired) | 991 | 2.37 | 34.6 | 814 |
| Unitek, Vita-VMK-68 Dentin-545 (vacuum-fired) | 947 | 2.42 | 35.2 | 792 |
| Hi-Life[4] for Microbond Restorations Body B-67 (vacuum-fired) | 1007 | 2.37 | 32.5 | 776 |
| Biobond Bocy-65 (vacuum-fired) | 990 | 2.39 | 31.2 | 650–? |

[1]Pelletized at 1,138 kg/cm² and subjected to standard 12 min. experimental air fire.
[2]The J. M. Ney Co., Bloomfield, Connecticut
[3]Columbus Dental Manufacturing Co., Columbus, Ohio
[4]Howmedica, Ltd., Chicago, Illinois
[5]Lot numbers given in Table XIII Dimensional change measurements are made on heating and cooling with ambient conditions under an applied stress of 120 g/cm$^2$. All porcelains are heated at 6° C./min to the same viscosity at temperatures not much above the softening point and then cooled at 6° C./min to temperatures below the strain point, and then cooled more slowly without furnace control to room temperature.

The linear dimensional change on the heating and cooling of current commercial body porcelains shows that the brands used for total non-aluminous porcelain constructions, like the classical air-firing Apco porcelain, have much lower coefficients of thermal expansion than typical metal-ceramic body porcelains. Neydium, V, B-1 (Ney Dental Co., Bloomfield, Conn.) has a higher softening point temperature than the Hi-Life, B-67 (Howmedica, Chicago, IL), and both these metal-ceramic porcelains have much higher thermal expansion coefficients than the Apco S-32 (Columbus Dental Manufacturing Co., Columbus, Ohio). Other metal-ceramic body porcelains have thermal-dimensional behavior similar to one another, e.g., Will-Ceram, B-81; Unitek VMK-68, Dentin-545, and Biobond, B-65.

Most of the inventive porcelains of this example are similar to Apco in thermal dimensional change characteristics. Therefore, these gel route prepared porcelains are most suitable to be fired on alumina preforms, over aluminous porcelain cores, or to be used for total porcelain constructions.

However, the use of some of these low alkali porcelains for metal-ceramic constructions is not to be precluded. The most significant factor determining thermal dimensional matching of porcelain to the substrate is the linear dimensional change which occurs below the strain point. This point probably is approximated by the point of flexure in the cooling curve where it becomes nearly linear on further cooling.

For example, the metal-ceramic porcelain Ceramco (lots prior to 1977) gingival B-81 heated at the standard 6° C./min rate and 120 g/cm$^2$ applied stress exhibits an average linear coefficient of dimensional change of $11.01 \times 10^{-6}/°C.$ over the interval 23° to 450° C. The two low alkali experimental frits which fire to form porcelains that approach closest to the linear change coefficient of Ceramco gingival are 82-2 and 86-2. Their coefficients of linear change on cooling are 9.03 and $9.79 \times 10^{-6}/°C.$, respectively.

It is to be noted that 82-2 has a point of flexure on the cooling curve of 475° C., slightly higher than the 450° temperature for this point with Ceramco gingival. When a standard 120 g/cm$^2$ specimen load is applied in the dilatometer, the deformation point of 82-2 fired porcelain is 606° C., apparently slightly lower than Ceramco's 617° C. Though 86-2 has a higher linear change coefficient on cooling, the temperature of flexure on its cooling curve is at 550° C. and its deformation point is 645° C., both at higher temperatures than for Ceramco gingival.

Both 82-2 and 86-2 mature in a standard 12 minute air fire at much lower temperatures, 845° and 885° C., respectively, than Ceramco gingival B-81 (991° C.) (Table XII). Several other inventive porcelains fabricated from gel prepared frit have points of flexure of 500° C. This is a much lower temperature than the point of flexure on the cooling curve of Apco S-32 of 550° C. (Table XIII).

Certainly, a low deformation temperature and a low strain point aid in fitting the fired porcelain coating to the substrate. The lower thermal expansion inventive porcelains, i.e., with coefficients of cooling of less than $9 \times 10^{-6}/°C.$, may be particularly suitable to be fired over sintered alumina preforms or on aluminous porcelain cores.

Low porcelain maturation temperatures reduce the range over which a metal substrate is heated and thereby minimize metal sag or creep. The low porcelain maturation temperature of the gel route prepared inventive porcelains makes it possible to use new alloys for dental bridgework which may have more desirable properties, e.g., ductility.

TABLE XIII

Deformation Temperature and Dimensional Change of Fired Porcelain

| Porcelain Description | Deformation Point, °C. | Coefficients of Linear Change, $\times 10^{-6}$ | | | | | |
|---|---|---|---|---|---|---|---|
| | | 23 to 450° C. | | 23 to 500° C. | | 23° C. to temperature at flexure of cooling curve | |
| | | Heating | Cooling | Heating | Cooling | Heating | Cooling |
| A. Commercial Porcelains | | | | | | | |
| Ceramco, Gingival B-81 Lot #1984 (1973) | 617 | 11.01 | 11.16 | 11.32 | 11.22 | to 450° C. 12.83 | 11.16 |
| Dentsply Biobond, Body B-65 Lot #293 (1972–1973) | 630 | 12.18 | 11.67 | 12.26 | 12.24 | to 450° C. 12.18 | 11.67 |
| Unitek, Vita Dentin, VMK-68 Dentin-545 Lot #206 (1972–1973) | 656 | 12.30 | | 12.58 | | | |
| Will Ceram, Body B-81 Lot #1984 (1973) | 683 | 13.65 | | 13.59 | | | |
| Howmetica Hi-Life Body B-67 Lot #749 | 675 | 13.54 | | 13.65 | | | |

TABLE XIII-continued
Deformation Temperature and Dimensional Change of Fired Porcelain

| | | | | | |
|---|---|---|---|---|---|
| (1972-1973) Neydium Y B-1 Lot #B0501 | 774 | 13.82 | 11.19 | 14.15 | 12.41 |
| (1978) Apco, S-32 Lot #99-13872 (1970-1971) | 710 | 8.48 | 8.27 | 8.34 | 8.25 |

B. Experimantal Porcelains With Low Alkali Contents

| | | | | | | |
|---|---|---|---|---|---|---|
| 60-1 | 720 | 6.98 | 8.38 | 6.86 | 8.24 | to 500° C. |
| (−200) | | | | | | 6.86    8.24 |
| 73-1 | 681 | 7.85 | 7.20 | 7.76 | 7.39 | to 500° C. |
| (−200 mesh) | | | | | | 7.76    7.39 |
| 79-2 | 656 | 7.87 | 8.26 | 7.90 | 8.41 | to 500° C. |
| (−140 mesh) | | | | | | 7.90    8.41 |
| 82-2 | 606 | 8.20 | 8.95 | — | — | to 475° C. |
| (−140 mesh) | | | | | | 8.30    9.03 |
| 85-2 | 617 | 8.55 | 8.22 | 8.28 | 8.33 | to 500° C. |
| (−140 mesh) | | | | | | 8.28    8.33 |
| 86-2 | 645 | 8.55 | 9.60 | 8.39 | 9.61 | to 550° C. |
| (−140 mesh) | | | | | | 8.20    9.79 |
| 88-1b | 734 | 8.20 | 8.34 | 8.07 | 8.23 | to 550° C. |
| (−140 mesh) | | | | | | 7.87    8.23 |

C. Experimental Porcelains With High Alkali Contents

| | | Coefficients of Linear Change, $\times 10^{-6}$ | | |
|---|---|---|---|---|
| Porcelain Description | Deformation Point | 23 to 450° C. Heating | 23 to 500° C. Heating | 23° C. to temperature of brittle fracture* Heating |
| 161-4 | 655 | 7.78 | | to 422° C. |
| (−140 mesh) | | | | 7.74 |
| 160-2 | 645 | 11.01 | 11.01 | to 450° C. |
| (−140 mesh) | | | | 11.01 |

*Same, in these materials, as the temperature at flexure cooling curve.

Most of the inventive porcelains with low-alkali contents and translucencies equal to or better than tooth have peak maturation temperatures and good form retention in the standard 12 minute gloss fire below those of the lowest temperature-maturing commercial porcelains. One of these, 80-3 (minus-140-mesh), has tooth translucency, a very good triple-point flexure strength of 996±50 kg/cm², and a 12 minute standard fire specimen maturation temperature of 940° C., slightly lower than that of Unitek's Vita dentin with a maturation temperature of 947° C. The solubility of this porcelain and its resistance to gloss reduction in 4 vol. % acetic acid solution is superior to half of the commercial dentin or body metal-ceramic porcelains (Table XIV A and B). However, this porcelain, when fired, does generate some milkiness which may or may not be aesthetically advantageous, depending upon the color shading desired.

Another porcelain with better translucency at maturity and no milkiness, 85-2, has a solubility performance and gloss retention in 4 vol. % acetic acid distinctly superior to the commercial Neydium V body porcelain. The 12 minute maturation temperature of this porcelain is only 885° C., much lower than any of the examined commercial porcelains.

Raw porcelains 82-2 and 86-2 mature in the standard 12 minute fire at 845° and 885° C., respectively, to better than tooth translucency with no milkiness. The mature porcelains have flexure strengths in the middle to lower range, 787 and 726±50 kg/cm². They have coefficients of linear dimensional change on cooling below the flexure point in the cooling curve of 9.03 and $9.79 \times 10^{-6}/°C.$, respectively.

TABLE XIV
Fired Porcelain Solubility
(One week in 4 vol. % acetic acid at 80 ± ¼° C.)
A. Commercial Porcelain

| Porcelain Description | Number of Specimens Tested | Mean Calculated Surface Area cm² | Mean Weight Loss mg/cm² | Gloss Retention (after testing) |
|---|---|---|---|---|
| Steele's Apco S-32, Lot # 99-13872 (1970-71) | 2 | 3.863 | 0.026 | Yes |
| Ceramco, Gingival B-81, Lot # 1984 (1973) | 25 | 3.863 | 0.037 | Yes |
| Howmetica HiLife Body B-63 (1972-1973) | 2 | 3.823 | 0.128 | Yes |
| Dentsply Biobond, Body B-65, Lot # 293 (1972-73) | 4 | 4.024 | 0.153 | No (slightly dull) |
| Unitek, Vita VMK-68 Dentin 545, Lot # 206 (1972-1973) | 3 | 3.874 | 0.181 | No (slightly dull) |
| Will Ceram Body B-81, Lot # 233 (1977) | 3 | 3.653 | 0.114 | Yes |

TABLE XIV-continued

| Neydium V Body B-1, Lot # B0501 (1978) | 30 | 3.452 | 5.382 | No (dull within 67 hours) |
|---|---|---|---|---|

Fired Porcelain Solubility
(168 hrs. in 4 vol. % acetic acid at 80 ± ½° C.)
B. Experimental Porcelains with Low Alkali Contents

| Porcelain Description | Specimen No. | Calculated Surface Area cm$^2$ | Weight Loss mg/cm$^2$ | Gloss Retention (after testing) |
|---|---|---|---|---|
| 6-1 (wet-mill long) | 686 | 3.545 | 0.127 | Yes |
| 80-3 (−140 mesh) | 684 | 4.011 | 0.137 | Yes |
| 23-1 (wet mill long) | 687 | 3.376 | 0.145 | No (moderate grainy) |
| 88-1b (−140 mesh) | 723 | 3.652 | 1.476 | Yes |
| 64-1 (−200 mesh) | 672 | 4.051 | 1.528 | No (slight reduction, pitted) |
| 89-1b (−140 mesh) | 689 | 3.873 | 1.973 | Yes |
| 90-1b (−140) | 693 | 3.891 | 2.258 | Yes |
| 84-2 (−140 mesh) | 680 | 4.025 | 2.629 | No (within 113 hrs pitted, slight gloss) |
| 60-1 (−200 mesh) | 690 | 3.573 | 2.707 | No (moderate) |
| 37-3(2) (−200 mesh) | 682 | 3.828 | 2.961 | No (dull) |
| 85-2 (−140 mesh) | 668 | 3.925 | 4.281 | No (dull within 1135 hrs) |
| 86-2 (−140 mesh) | 669 | 4.150 | 6.944 | No (slight very pitted) |
| 78-1b (140 mesh) | 685 | 3.970 | 8.977 | No (moderate stained & pitted) |
| 87-1b (−140 mesh) | 683 | 3.995 | 13.728 | No (slight extremely pitted) |
| 73-1 (−200 mesh) | 688 | 3.792 | 20.375 | No (dull within 122 hrs) |

If combined with a very low deformation temperature and strain point, these linear coefficients of change may not be prohibitive. Formulation 82-2 appears particularly promising because its deformation point under an applied stress of 120 g/cm$^2$ and 6° C./min heating rate in ambient air, 606° C., is below both of the two examined commercial porcelains with lowest deformation points, Ceramco and Biobond gingival and body porcelains (617° and 630° C., respectively). Also the temperature of the point of flexure in the fired 82-2 is the same as for Ceramco. But the use of a low alkali porcelain like 82-2 may be prohibitive without the application of a very thin relatively insoluble glaze. Because of reduced surface oxidation, low-temperature maturing core porcelains with low-alkali contents may prove to offer better compensation with the base-metal alloys, even though their thermal expansion is lower than current commercial metal-ceramic porcelains.

Ceramco B-81, a gingival or body metal-ceramic porcelain, attains maturity in a standard 12 minute air fire at a peak specimen temperature of 991° C. Minus-140-mesh frit has been prepared by the gel route of essentially the same composition as the Ceramco gingival, but much coarser grained, which in the standard fire matures 70° C. lower than the Ceramco at a specimen peak temperature of 917° C. (#160). None of the common low-fusing commercial body porcelains has been observed to mature this low in the standard 12 minute gloss fire. The lowest fusing commercial porcelain is Unitek's VMK-68, Dentin 545, which matures in the 12 minute standard fire at a specimen peak temperature of 947° C.

The substitution of 4 mole percent Li$_2$O for half of the 8.1 mole percent K$_2$O of the Ceramco gingival composition (#160) prepared by the gel route, results in lowering the specimen maturation temperature to 873° C. and increasing the translucency (#161). Substitution of only two mole percent Li$_2$O for equal moles of Na$_2$O in experimental porcelain composition #162 results in a slight raising of the peak maturation temperature to 920° C. over the 917° C. obtained with the Ceramco gingival gel route prepared porcelain frit (#160-2). The two mole percent Li$_2$O substitution in #162 does result in an increase in translucency over fired porcelain constructed from gel route prepared frit of the Ceramco gingival composition, 160-2, but with less milkiness. Also, the two mole percent Li$_2$O substituted porcelain 162-2 is less milky than the four mole percent Li$_2$O substituted porcelain 161-4.

The coefficients of thermal expansion and contraction of the high alkali experimental products are 10 to 20% less than the lowest expanding metal-ceramic porcelain. Commercial Ceramco gingival on heating to the temperature of flexure in the cooling curve 450° C. has a linear coefficient of dimensional change of 11.01×10$^{-6}$/°C. The Ceramco oxide formulation prepared by the gel route has approximately the same temperature for this point on the cooling curve, 450° C., with the same coefficient of expansion to this temperature of 11.01×10$^{-6}$/°C. Biobond body porcelain heated to about the same temperature, 450° C., has a coefficient of linear expansion closer to this experimental porcelain value, 12.18×10$^{-6}$/°C. For the four mole percent Li$_2$O substituted porcelain, 161-4, the point of flexure is 422° C., and the coefficient of linear expansion to this temperature is 7.74×10$^{-6}$/°C.

Flexure points on the cooling curves of Ceramco gingival, Biobond body and Howmedica's Hi-Life body are close to or at the temperature of brittle fracture on the cooling curve. This relationship appears to hold for the high-alkali, high thermally expanding inventive porcelain.

It is to be noted that for one of the low alkali inventive porcelains, 82-2, the flexure point on cooling is 475° C. and for several others, 500° C., much lower than the commercial porcelain of similar expansion, Apco, with a flexure point temperature on the cooling curve of 550° C. In all porcelains it is expected that lowering of this point would correspond to lowering the strain point where brittle fracture may be expected under slow relaxed cooling. Lowering of these temperatures is expected to be desirable for easing frit to the substrate over which porcelains might be fired. If more compression is desired the thermal expansion may be lowered.

Form retention data shows that experimental porcelain fabricated from gel route prepared frit retain their form at maturity as well as current commercial non-aluminous porcelains (Table XV). It is particularly promising that high-alkali experimental porcelain with four mole percent Li$_2$O substituted for equal moles of $K_2O$ (161-4) has an exceptionally good form retention on the mature porcelain cylinder of 0.948.

TABLE XV

Fired Porcelain Solubility
(One week in 4 vol. % acetic acid at 80 ± ¼° C.)
A. Commercial Porcelain

| Porcelain | Number of Specimens Tested | Mean Calculated Surface Area cm² | Mean Weight Loss mg/cm² | Gloss Retention (after testing) |
|---|---|---|---|---|
| Steele's Apco, S-32, Lot #99 13872 (1970-71) | 2 | 3.863 | 0.026 | Yes |
| Ceramco, Gingival B-81, Lot #1984 (1973) | 25 | 3.863 | 0.037 | Yes |
| Howmet, Hi-Life Body B-63 (1972-1973) | 2 | 3.823 | 0.128 | Yes |
| Dentsply Biobond Body B-65 Lot #293 (1972-73) | 4 | 4.024 | 0.153 | No (slightly dull) |
| Unitek, Vita VMK-68 Dentin 545 Lot #206 (1972-1973) | 3 | 3.874 | 0.181 | No (slightly dull) |
| Will Ceram Body B-81 Lot #233 (1977) | 3 | 3.653 | 0.114 | Yes |
| Neydium V Body B-1 Lot #B0501 (1978) | 30 | 3.452 | 5.382 | No (dull within 67 hours) |

Fired Porcelain Solubility
(168 hrs. in 4 vol. % acetic acid at 80 ± ¼° C.)
B. Experimental Porcelains with Low Alkali Contents

| Porcelain Description | Specimen No. | Calculated Surface Area cm² | Weight Loss mg/cm² | Gloss Retention (after testing) |
|---|---|---|---|---|
| 6-1 (wet-mill long) | 686 | 3.545 | 0.127 | Yes |
| 80-3 (−140 mesh) | 684 | 4.011 | 0.137 | Yes |
| 23-1 (wet mill long) | 687 | 3.376 | 0.145 | No (moderate grainy) |
| 88-1b (−140 mesh) | 723 | 3.652 | 1.476 | Yes |
| 64-1 (−200 mesh) | 672 | 4.051 | 1.528 | No (slight reduction, pitted) |
| 89-1b (−140 mesh) | 689 | 3.873 | 1.973 | Yes |
| 90-1b (−140) | 693 | 3.891 | 2.258 | Yes |
| 84-2 (−140 mesh) | 680 | 4.025 | 2.629 | No (within 113 hrs pitted, slight gloss) |
| 60-1 (−200 mesh) | 690 | 3.573 | 2.707 | No (moderate) |
| 37-3(2) (−200 mesh) | 682 | 3.828 | 2.961 | No (dull) |
| 85-2 (−140 mesh) | 668 | 3.925 | 4.281 | No (dull within 1135 hrs) |
| 86-2 (−140 mesh) | 669 | 4.150 | 6.944 | No (slight very pitted) |
| 78-1b (140 mesh) | 685 | 3.970 | 8.977 | No (moderate stained & pitted) |

TABLE XV-continued

| | | | | |
|---|---|---|---|---|
| 87-1b (−140 mesh) | 683 | 3.995 | 13.728 | No (slight extremely pitted) |
| 73-1b (−200 mesh) | 688 | 3.792 | 20.375 | No (dull within 122 hrs) |

Fired Porcelain Solubility
(168 hrs. in 4 vol. % acetic acid at 80 ± ¼° C.)
C. Experimental Porcelains with High Alkali Contents

| Porcelain Description | Specimen No. | Calculated Surface cm² | Weight Loss mg/cm² | Gloss Retention (after testing) |
|---|---|---|---|---|
| 161-4 (−140 mesh) | 756 | 3.907 | 0.051 | Yes |
| 162-2 (−140 mesh) | 759 | 3.746 | 0.091 | Yes |
| 156-2 (−140 mesh) | 737 | 3.865 | 0.250 | Yes |
| 160-2 (−140 mesh) | 753 | 3.892 | 0.272 | Yes |
| 159-2 (−140 mesh) | 749 | 4.038 | 4.262 | No (dull within 50 hrs) |
| 167-3 (−140 mesh) | 839 | 3.842 | 0.135 | Yes |
| 165-3 (−140 mesh) | 830 | 3.796 | 2.272 | No |

The ability of the low-alkali experimental porcelain bars to retain form over a wide range in firing condition appears in general to equal or exceed that of current commercial porcelains. As with the low-alkali porcelains, firing shrinkages for the high-alkali porcelains except for 159-4 and 160-2, which show slight bloating with firing shrinkages of 26 and 28 vol. %, respectively, are within the range of identically pelletized commercial fired porcelains, e.g., in volume percent, 156-2, 33.5; 161-4, 33.5; and 162-2, 32.2. Fired densities of porcelain bars of the slightly bloated high-alkali porcelains 159-4, and 160-2, are low, 2.17 and 2.13 g/cm³, respectively. The other high-alkali fired inventive porcelain bars have relatively high densities as compared to the low-alkali porcelains made from minus-140 mesh gel route prepared frit, e.g., in g/cm³, 156-2, 2.31; 161-4, 2.27; and 162-2, 2.33.

In general, for the low-alkali porcelains, the maturation temperature is lower the lower the $Al_2O_3$ to $B_2O_3$ mole ratio.

EXAMPLE 4 (COMPARATIVE EXAMPLE)

Porcelain frits with the compositions indicated in Table XVI are prepared. Gelling is followed by hot-air drying, 700° C. defuming and calcination to temperatures as high as 1000° C. and grinding through 140-mesh.

Many experimental frits appear especially promising for metal-ceramic application. The properties of these experimental porcelains are shown in Table XVII, A. One, a 926° C. calcined frit (165-3), fires to porcelains which have nearly the same thermal expansion and translucency as B-62 Biobond body (1978, Lot A 86, Table XVII, B) porcelain, $12.10 \times 10^{-6}$/°C. ($\pm 0.1 \times 10^{-6}$/°C.) between 23° and 400° C., and the same deformation temperature, under a 1.165-1.188 g/mm² applied stress (613°-630° C.).

Another frit calcined at 1000° C. (194-7) produces a porcelain with a thermal expansion (23°-400° C.) of $12.90 \times 10^{-6}$/°C. Whereas Ceramco B-65 gingival (1978, Lot 3040, Table XVII, B) has a fusion temperature in a standard 12 min. air fire of 965° C., this experimental porcelain fuses much lower at 908° C. Its deformation temperature, 578° C., is slightly lower than that of Ceramco gingival, 594°–604° C.

Slump factors have been measured on some experimental porcelains. For example, 165 and 167 calcined frits have a slump factor of 0.90, slightly better than the Biobond body's 0.87 and about that of Ceramco gingival's 0.91 (B-81, Table XIV). The respective firing shrinkages for 165 and 167; are 32.1 and 31.9 vol. %. This compares with the respective air-fired values of Ceramco gingival and Biobond body (B-65, Table XIV) of 34.6 and 31.2 vol. %.

TABLE XVI

EXPERIMENTAL PORCELAIN FRIT COMPOSITIONS
WEIGHT PERCENT

| Frit No | $SiO_2$ | $Al_2O_3$ | $B_2O_3$ | $K_2O$ | $Na_2O$ | $Li_2O$ | CaO |
|---|---|---|---|---|---|---|---|
| 165 | 58.03 | 16.73 | 3.84 | 10.50 | 8.84 | | 2.06 |
| 167 | 63.06 | 13.58 | 5.93 | 11.45 | 5.45 | 0.53 | |
| 194 | 59.76 | 17.51 | 1.50 | 10.99 | 9.25 | 0.99 | |

TABLE XVII

A. EXPERIMENTAL PORCELAIN PROPERTIES

| Frit No. | Fusion Temp. °C. | Translucency $C_{0.70}$ | Solubility mg/cm$^2$ | Flexural Strength kg/cm$^2$ | Deformation Temp., °C. | Coefficient Of Thermal Expansion 23 to 400° C., × $10^{-6}$/°C. |
|---|---|---|---|---|---|---|
| 165-3 | 926–928 | 0.25–0.30 (928)+ | 3.008 (928)+ | 684 (927)+ 619 (929) | 613 (926)+ 630 (926) | 12.10 11.09 |
| 167-3 | 914–917 | 0.30–0.35 (917)+ | 0.135 (917)+ | 799 (916) | 637 (915) 611 (916) 614 (917) | 8.54# 8.66 8.09 |
| 194-7 | 908 | 0.35–0.40 (923) | 0.481 (923) | 757* (919) 860* (922) 746* (924) | 578 (923) | 12.90 |
| 161-4 | 871 | n.d. | 0.051 (871) | n.d. | 581 (871) 598 (872) | 7.53 7.69 |

B. COMMERCIAL PORCELAIN PROPERTIES

| Frit Designation | Fusion Temp., °C. | Translucency, $C_{0.70}$ (±0.05) | Solubility, mg/cm$^2$ | Flexure Strength, kg/cm$^2$ | Deformation Temp., °C. | Coefficient of Thermal Expansion 23 to 400° C. × $10^{-6}$/°C. |
|---|---|---|---|---|---|---|
| Ceramco (air fired) gingival, B-62, 1972–1973 Lot #946 | 991 | 0.20–0.25 (1009)+ | 0.066 (995)+ 0.044 (1009) | 585 (991)+ 779 (1012) 507* (1040) | 606 (994)+ 604 (1007) 592 (1051) | 12.25# 10.79 10.90 |
| Ceramco (vacuum) gingival, B-81, 1973 Lot #1984 | 991 | 0.25–0.30 (990) | 0.016–0.063 (998–1005) | 759 (975) 807 (983) 814 (991) 693 (1012) 646 (1018) 764 (1035) | 616 (992) | 10.69 |
| Ceramco (vacuum) gingival, B-65, Spring 1978 Lot #2814 | 965 | 0.25–0.30 (994) 0.25–0.30 (995) | 0.011–0.039 (994–995) | 710 (994) | | |
| Ceramco (vacuum) gingival, B-65, Oct., 1978 Lot #3040 | 965 | 0.35–0.40 (965) 0.35–0.40 (995) | 0.027–0.052 (965–997) | 720 (965) 622 (992) 674 (995) 626 (996) 689 (996) | 604 (965) 594 (995) | 11.93 10.95 |
| Ceramco (vacuum) gingival, G-Al, 1980 Lot #3626 | 963 | | | | | |
| Ceramco (vacuum) incisal, B-E.Z. light, 1972–1973 Lot #2404 | 978 | 0.30–0.35 (982) 0.30–0.35 (1000) | 0.021 (982) 0.022 (982) 0.008 (1000) 0.021 (1000) | 731 (978) 774* (991) 641* (1000) | 610 (980) | 11.24 |
| Ceramco (vacuum) incisal, G-50, 1980 Lot #3622 | 964 | | | | | |
| Ceramco (vacuum) opaque, B.F.-68, | | | | | 638 (1030) 625 (1031) | 10.82 10.15 |

TABLE XVII-continued

| | | | | | | |
|---|---|---|---|---|---|---|
| 1972–1973 Lot #888 | | | | | | |
| Ceramco (vacuum) Paint-o-pake B-65, 1972–1973 Lot #2788 | | | | | 675 (1033) | 11.27 |
| Biobond (vacuum) body, B-65, 1972–1973 Lot #293 | 990 | 0.30–0.35 (1018) | 0.124–0.200 (989–1020) | 604 (965) 557 (977) 654 (990) 662 (992) 618 (1003) 457 (1017) 597 (1025) | 645 (1019) 629 (1020) | 11.01 11.67 |
| Biobond (vacuum) body, B-62, 1978 Lot #A86 | 982 | | | 706 (982) | 615 (983) | 12.03 |
| Biobond (vacuum) opaque, O-2, 1972–1973 Lot #985 | | | | | 715 (1021) | 11.04 |
| Micro-Bond Hi-Life (vacuum) body, B-67, 1972–1973 Lot #749 | 1004 | 0.30–0.35 (1006)+ | 0.123 (1006)+ 0.133 (1006) | 558 (975)+ 736 (991) 605 (1000) 708 (1004) 776 (1006) 653 (1043) 688 (1055) | 656 (1005)+ 649 (1007) 664 (1008) | 13.48# 13.08 12.73 |
| Micro-Bond Hi-Life (vacuum) body, unstained, 1972–1973 Lot #80 | 992 | 0.25–0.30 (991) | 0.174 (991) | 524 (992) 686 (1008) 723 (1008) 618* (1020) 734* (1031) | 650 (1021) | 12.21 |
| Micro-Bond Hi-Life (vacuum) body, unstained, B-85 1979 Lot #061979 | 985 | 0.20–0.25 (974) | 0.097–0.138 (985) 0.075–0.096 (1009) | 656 (985) | 617 (984) 599 (985) 606 (985) | 13.12 13.26 13.44 |
| Neydium V (vacuum) body, B-1, 1978 Lot #B0501 | 1002 | 0.25–0.30 (1000) 0.30–0.35 (1002) 0.25–0.30 (1012) | 4.872–6.182 (1000–1019) | (1008–1101 (934) 988 (965) 1048 (998) 868 (1000) 1011 (1006) 943 (1010) 871 (1014) 1026 (1040) | | |
| Neydium V (vacuum) incisal, V-1, 1978 Lot #10104 | 1004 | 0.30–0.35 (999) | 5.118 (999) | 985 (1004) | | |
| Vita VMK-68 (vacuum) dentin-545, 1972–1973 Lot #206 | 947 | 0.30–0.35 (947) | 0.198 (947) 0.226 (947) | 827 (922) 792 (947) 857 (960) 804 (978) 698 (992) | 665 (947) 650 (947) | 11.84 11.88 |
| Vita VMK-68 (vacuum) dentin-547, 1980 Lot #251 | 949.5 | | | 779 (949.5) | 631 (947) | 11.97 |
| Vita VMK-68 (vacuum) enamel-559, 1972–1973 | 949 | 0.30–0.35 (990) | 0.144 (989) 0.217 (990) | 789 (980) 818* (989) | 643 (990) | 11.03 |
| Vita VMK-68 (vacuum) enamel-559, 1977 Lot #398 | 949 | | 0.216 (948) | 762 (947) 859 (949) 845 (949) | | |
| Vita VMK-68 (vacuum) enamel-557, 1980 Lot #768 | | 0.234 | (935) | | | |

TABLE XVII-continued

| | | | | | | |
|---|---|---|---|---|---|---|
| Vita-VMK-68 (vacuum) enamel-532, 1972–1973 | | | | | 815 (959) | 12.73 |
| Will-Ceram body, B-81, 1977 Lot #0233 | 971 | | 0.218 (974)+ 0.240 (977) 0.216 (979) | 720 (939.5)+ 713 (951) 622 (960) 851 (964) 772 (964) 761 (964) 727 (971) 833 (971) 730 (974) 928 (975) 1053 (990) 891 (1014) 905 (1062) | 660 (971)+ 654 (976) 666 (976) 660 (984) | 13.62# 13.29 13.10 13.23 |
| Will-Ceram incsal, E-2, 1977 Lot #0236 | 974 | 0.20–0.25 (971)+ 0.30–0.35 (982) | 0.124 (971) 0.111 (982) 0.106 (999) | 757 (974) 777 (976) 618 (977) 711 (980) 557* (985) 866* (999) | 587 (996) | 10.21 |
| Will-Ceram opaque, O-6, 1977 Lot #0232 | | | | | 715 (998) | 12.94 |
| Steele's Apco (air fired) S-32, 1970–1971 Lot #99-13872 | 1025 | 0.20–0.25 (1026) | 0.025 (1025) 0.026 (1028) | 622 (1008) 817 (1025) 850 (1073) | | |
| Steele's Apco (air fired) s-32, 1970–1971 Lot #99-229972 | 1025 | 0.25–0.30 (1027) | 0.028 (1027) | | | |
| Steele's Aluminous (air fired) body, D-5 pink, 1972–1973 | 979 | 0.30–0.35 (997) | 0.252 (997) | 1044 (979) 845* (994) 715* (995) 715* (996) | | |
| Steele's Aluminous (air fired) core, HEC-25 (yellow), 1972–1973 | | | | 1418* (1130) | | |
| Steele's Aluminous (air fired) enamel, AE-2 (white), 1972–1973 | 979 | 0.15–0.20 (980) 0.15–0.20 (983) | 0.296 (980) | 712* (979) 923 (979) 685* (979) | | |

C. Application and Apparent Density of Commercial Porcelains
(as obtained with 12 min. air fire)

| Frit Designation | Atmosphere (porcelain type) | Application Device | Zone | Density, g/cm³ |
|---|---|---|---|---|
| Ceramco, B-62 1972–1973 Lot #946 | air | metal-ceramic | body (gingival) | 2.32–2.34 |
| Ceramco, B-81 1973 Lot #1984 | vacuum | metal-ceramic | body (gingival) | 2.36–2.38 |
| Ceramco, B-65 1978 Lot #2814 | vacuum | metal-ceramic | body (gingival) | 2.36–2.37 |
| Ceramco, B-65 1978 Lot #3040 | vacuum | metal-ceramic | body (gingival) | 2.36 |
| Ceramco, B.E-Z. light 1972–1973 Lot #2404 | vacuum | metal-ceramic | enamel (incisal) | 2.34–2.35 |
| Ceramco, B.F.-68 1972–1973 Lot #888 | vacuum | metal-ceramic | opaque | 2.61–2.63 |
| Ceramco, B.F.-68 paint-o-pake, | vacuum | metal-ceramic | opaque | 2.84 |

TABLE XVII-continued

| | | | | |
|---|---|---|---|---|
| B-65 1972–1973 Lot #2788 | | | | |
| Biobond, B-65 1972–1973 Lot #293 | vacuum | metal-ceramic | body | 2.35–2.37 |
| Biobond, B-62 1978 Lot #A86 | vacuum | metal-ceramic | body | 2.37–2.38 |
| Biobond, O-2 1972–1973 Lot #985 | vacuum | metal-ceramic | opaque | 2.56 |
| Micro-Bond Hi-Life 1972–1973 Lot #749 | vacuum | metal-ceramic | body | 2.34–2.36 |
| Micro-Bond Hi-Life unstained, 1972–1973 Lot #80 | vacuum | metal-ceramic | body and enamel | 2.34–2.37 |
| Micro-Bond Hi-Life unstained, B-85, 1979 Lot #061979 | vacuum | metal-ceramic | body and enamel | 2.31–2.33 |
| Neydium V, B-1, 1978 Lot #B0501 | vacuum | metal-ceramic | body | 2.40–2.42 |
| Neydium V V-1, 1978 Lot #I0104 | vacuum | metal-ceramic | enamel (incisal) | 2.42–2.43 |
| Neydium V B-1, 1978 | vacuum | metal-ceramic | opaque | 2.60 |
| Vita VMK-68 dentin-545 1972–1973 Lot #206 | vacuum | metal-ceramic | body (dentin) | 2.42–2.43 |
| Vita VMK-68 dentin-547 1980 Lot #251 | vacuum | metal-ceramic | body (dentin) | 2.40–2.41 |
| Vita VMK-68 enamel-559 1972–1973 | vacuum | metal-ceramic | enamel | 2.39–2.41 |
| Vita VMK-68 enamel-559 1977 Lot #398 | vacuum | metal-ceramic | enamel | 2.41–2.42 |
| Vita VMK-68 enamel-557 1980 Lot #768 | vacuum | metal-ceramic | enamel | 2.42 |
| Will-Ceram B-81, 1977 Lot #0233 | vacuum | metal-ceramic | body | 2.44–2.45 |
| Will-Ceram E-2, 1977 Lot #0236 | vacuum | metal-ceramic | enamel | 2.42–2.43 |
| Will-Ceram O-6, 1977 Lot #0232 | vacuum | metal-ceramic | opaque | 2.60 |
| Steele's Apco S-32 1970–1972 Lot #99-13872 | air | jacket-crown | body | 2.30–2.31 |
| Steele's Apco S-32 1970–1972 Lot #99-229972 | air | jacket-crown | body | 2.30 |
| Steele's Aluminous, D-5 1972–1973 | air | jacket-crown | body | 2.35–2.36 |
| Steele's Aluminous, AE-2 1972–1973 | air | jacket-crown | enamel | 2.30 |

+Number in parentheses ( ) was the peak temperature at which the specimen was fired in air for 12 minutes.
Specimen temperature is the same as specimen listed in deformation temperature column.
*Specimen was ground to nonstandard dimensions. Bar was less thick and less wide than normal.

The solubility of fired experimental porcelain 167-3 after 7 days in 4 vol. % acetic acid solution at 80° C. is 0.135 mg/cm², essentially the same as Biobond body's 0.153 mg/cm², but not as good as Ceramco gingival's 0.037 mg/cm² (Table XIV, A). Solubility of 165-3 is 2.272 mg/cm², greater than the above but much less than Ney's Neydium V body (B-1), which has a weight loss of 5.38 mg/cm² (Table XIV, A).

One 877° C. calcined lithium-containing porcelain, 161-4, with tooth translucency has as thermal expansion of 7.53 to 7.69×10⁻⁶/°C. (23°–400° C.). Its low fusion temperature of 871° C. should minimize the excessive oxidation encountered on heating which may weaken the porcelain to metal bond. The form retention of this porcelain is as good as any current commercial porcelain, and its solubility of 0.051 mg/cm² is about that of Ceramco B-81. Fired density and firing shrinkage of the minus-140-mesh frit are 2.27 g/cm³ and 3.5 vol. %. The deformation point is 581° to 598° C.

The combination in 161-4 of a low fusion temperature and solubility, high form retention and a thermal expansion lower than that of metal-ceramic body porcelains may make it suitable for use as a strengthening glaze. As such, it would act to strengthen an underlying body porcelain with a greater coefficient of expansion by causing limited compression thereof.

EXAMPLE 5

A gel which is peptized by solubilized carbonate ions, rather than by nitric acid in water solution, is prepared by first dissolving in 100 cc distilled water the following substances in grams: $H_3BO_3$, 0.666; $K_2CO_3$, 4.032; $Na_2CO_3$, 3.956; $Li_2CO_3$, 0.609. A mixture of 46.4 cm³ Ludox 130 M (DuPont de Nemours and Co., Wilmington, DE) and 6.85 cm³ 5025 alumina sol (Hammil and Gillespie, New York, NY) is then added quickly to the above carbonate solution under rapid stirring in a 200 cm³ narrow neck beaker. The Ludox 130 M contains in weight percent $SiO_2$, 26.17 and $Al_2O_3$, 4.03, and has a solution density at 23° C. of 1.23 g/cm³. the 5025 sol contains 22.62% $Al_2O_3$ and has a density at 23° C. of 1.34 g/cm³.

Excess water is evaporated from the above solution and slurry on a hot plate until a gel is formed. Gel is allowed to harden under the covered 2000 cc beaker for 26 days and is then placed in a number 10 wide mouth crucible (O.D. top, 86 mm; O.D. bottom, 32 mm and ht. 53 mm) and heated over a period of 2 hours, 55 min. in a Lindberg muffle furnace to a peak temperature of 802° C., and is then air quenched. The sample is then subsequently heat treated at 825° C. for one hour and then fritted at 1200° C. for one half hour, water quenched and then stage ground through 140 mesh. To anneal frit grain, the ground produce is heat treated at 600° C. for a half hour. Frit ground through various mesh sizes finer than 140 is used to fabricate fired porcelain specimens.

The porcelain frit has the following composition in weight percent: $SiO_2$, 59,757; $Al_2O_3$, 17.511; $B_2O_3$, 1.500; $K_2O$, 10.994; $Na_2O$, 9.253; and $Li_2O$, 0.985.

EXAMPLE 6 (COMPARATIVE EXAMPLE)

Porcelain frits with the compositions indicated in Table XVIII are prepared. Gelling is followed by hot-air drying, 700° C. defuming and calcination to temperatures as high as 1000° C.

TABLE XVIII

Experimental Porcelain Frit Compositions, WeightPercent (Calculated)

| Frit No. | SiO₂ | Al₂O₃ | B₂O₃ | K₂O | Na₂O | Li₂O | Rb₂O | Cs₂O | CuO | MgO | BaO | SrO | ZnO | SnO₂ | Y₂O₃ | La₂O₃ | Yo₂O₃ |
|---|---|---|---|---|---|---|---|---|---|---|---|---|---|---|---|---|---|
| 167 | 63.06 | 13.58 | 5.93 | 11.45 | 5.45 | 0.53 | | | | | | | | | | | |
| 183 | 60.74 | 17.51 | 1.50 | 8.32 | 7.00 | 4.93 | | | | | | | | | | | |
| 184 | 60.75 | 17.51 | 1.50 | 9.92 | 8.35 | 1.97 | | | | | | | | | | | |
| 185 | 59.25 | 17.08 | 3.92 | 10.20 | 8.59 | 0.96 | | | | | | | | | | | |
| 186 | 57.97 | 16.71 | 6.00 | 9.98 | 8.40 | 0.94 | | | | | | | | | | | |
| 187 | 60.87 | 17.47 | 1.49 | 10.95 | 9.22 | | | | | | | | | | | | |
| 188 | 59.36 | 17.04 | 3.91 | 10.69 | 9.00 | | | | | | | | | | | | |
| 190 | 60.81 | 17.40 | 1.50 | 10.44 | 8.78 | 0.98 | | | | | | | | | | | |
| 192 | 56.00 | 16.71 | 6.00 | 10.49 | 8.83 | 1.88 | | | | | | | | | | | |
| 194 | 59.76 | 17.51 | 1.50 | 10.99 | 9.25 | 0.99 | | | | | | | | | | | |
| 195 | 59.76 | 17.51 | 1.50 | 10.99 | 9.25 | 0.99 | | | | | | | | | | | |
| 196 | 58.29 | 17.08 | 3.92 | 10.72 | 9.03 | 0.96 | | | | | | | | | | | |
| 197 | 58.77 | 17.08 | 3.92 | 10.72 | 9.03 | 0.48 | | | | | | | | | | | |
| 198 | 57.61 | 14.63 | 2.91 | 10.22 | 14.63 | | | | | | | | | | | | |
| 200 | 60.26 | 17.51 | 1.50 | 10.99 | 9.25 | 0.40 | | | | | | | | | | | |
| 201 | 57.61 | 14.63 | 2.91 | 14.63 | 10.22 | | | | | | | | | | | | |
| 202 | 57.11 | 14.63 | 2.91 | 14.63 | 10.22 | 0.50 | | | | | | | | | | | |
| 203 | 57.61 | 14.63 | 1.91 | 12.22 | 10.63 | | | | | | | 2.00 | | | | | |
| 204 | 58.11 | 14.63 | 3.91 | 11.22 | 10.63 | 0.50 | | | | | | 1.00 | | | | | |
| 205 | 57.61 | 14.63 | 2.91 | 9.20 | 13.17 | | 2.48 | | | | | | | | | | |
| 206 | 57.61 | 14.63 | 2.91 | 9.20 | 13.17 | | | 2.48 | | | | | | | | | |
| 207 | 57.61 | 14.63 | 2.91 | 9.81 | 14.04 | | 0.50 | 0.50 | | | | | | | | | |
| 208 | 57.62 | 14.63 | 2.91 | 8.99 | 12.87 | 0.50 | 1.24 | 1.24 | | | | | | | | | |
| 209 | 57.62 | 14.63 | 2.91 | 10.02 | 11.65 | 0.50 | 1.00 | 1.00 | 0.05 | 0.02 | 0.50 | 0.10 | | | | | |
| 210 | 57.62 | 14.63 | 2.91 | 10.02 | 10.40 | 0.25 | 1.25 | 1.25 | 0.05 | 0.02 | 1.00 | 0.10 | | 0.50 | | | |
| 211 | 61.00 | 12.85 | 5.74 | 11.08 | 3.47 | 0.43 | 1.36 | 2.04 | 0.96 | | 0.45 | | | 0.62 | | | |
| 212 | 75.39ᵃ | 9.78 | 4.27 | 4.18 | 3.92 | 1.29 | | | 0.71 | | | | | 0.46 | | | |
| 213 | 72.66ᵃ | 10.86ᵇ | 4.74 | 4.64 | 4.35 | 1.43 | | | 0.80 | | | | | 0.52 | | | |
| 214 | 72.66ᵃ | 10.86ᶜ | 4.74 | 4.64 | 4.35 | 1.43 | | | 0.80 | | | | | 0.52 | | | |
| 215 | 75.39ᵈ | 9.78 | 4.27 | 4.18 | 3.92 | 1.29 | | | 0.71 | | | | | 0.46 | | | |
| 216 | 60.18 | 12.74 | 5.66 | 12.46 | 3.59 | 0.21 | 2.67 | 2.02 | 0.04 | 0.03 | 0.11 | 0.07 | | 0.22 | | | |
| 228 | 60.74 | 17.51 | 1.50 | 9.93 | 8.35 | 1.97 | | | | | | | | | | | |
| 229 | 60.81 | 17.49 | 1.50 | 10.44 | 8.78 | 0.98 | | | | | | | | | | | |
| 231 | 61.00 | 12.85 | 5.00 | 14.48 | 3.47 | 0.43 | | | 0.96 | 0.25 | 0.45 | 0.10 | 0.39 | 0.62 | | | |
| 235 | 58.23 | 12.26 | 5.48 | 13.26 | 4.15 | 0.52 | 1.62 | 2.45 | 0.96 | | 0.45 | | | 0.62 | | | |
| 244 | 57.70 | 14.65 | 2.91 | 9.83 | 13.60 | | 0.50 | 0.50 | | | | | | | | | 0.31 |
| 245 | 66.85 | 13.83 | 1.60 | 8.11 | 5.55 | | | | 0.08 | 0.26 | 3.72 | | | | | | |

TABLE XVIII-continued

Experimental Porcelain Frit Compositions, Weight Percent (Calculated)

| Frit No. | SiO$_2$ | Al$_2$O$_3$ | B$_2$O$_3$ | K$_2$O | Na$_2$O | Li$_2$O | Rb$_2$O | Cs$_2$O | CuO | MgO | BaO | SrO | ZnO | SnO$_2$ | Y$_2$O$_3$ | La$_2$O$_3$ | Yo$_2$O$_3$ |
|---|---|---|---|---|---|---|---|---|---|---|---|---|---|---|---|---|---|
| 263 | 59.76 | 17.21 | 1.50 | 10.99 | 9.25 | 0.99 | | | | | | | | 0.10 | 0.10 | 0.10 | |

[a] Cristobalite, minus-200 mesh-HCl leached, roasted 525° C. (1 hour) was added to gelling mixture as a nonsolubilized source of SiO$_2$. The following weight percents of the calcined frit were added as a water-free oxide:
Frit No. 212 used 30.00 wt %
Frit No. 213 used 32.34 wt %
Frit No. 214 used 33.34 wt %
Frit No. 215 used 15.00 wt %
[b] Fused alumina 0.05 μm, was added to gelling mixture as a nonsolubilized source of Al$_2$O$_3$. 2.39 percent by weight of the calcined frit was added as a water-free oxide.
[c] Hydrated alumina, 34.30 weight percent H$_2$O, was added to gelling mixture as a nonsolubilized source of Al$_2$O$_3$. The calcined frit contained 2.39 percent by weight as a water-free oxide of alumina.
[d] In addition to cristobalite (see footnote a), Frit No. 215 contained Supersilicia-HCl leached, roasted 520° C. (1 hour) as a nonsolubilized SiO$_2$ source in the gelling mixture. 15.00 percent by weight of the calcined frit was added as a water-free oxide.

Most of the calcined frits are then melted in platinum foil by holding at the peak temperature for thirty minutes. The peak temperature is determined by heating the frit in steps of 50° C., holding for thirty minutes, quenching the frit in water and examining the frit for the appearance of fine bubbles. When the quenched melt appears free of fine bubbles, the frit is stage ground and passed through a 140-mesh screen. The precise calcination and melt conditions of these frits are shown in Table XIX.

The properties of the frits prepared by melting (Table XX) differ significantly from the properties of the frits not processed beyond calcination. First, the melted frits fire into porcelains that are generally denser than those made from unmelted frits. This effect is evident by comparing the density of porcelain derived from frit 194-7 (2.23 to 2.36 g/cm$^3$) with that made from frit 194-8 (2.36 to 2.38 g/cm$^3$). Frits 194-7 and 194-8 are both from the same calcine, the only difference between them being that 194-8 was subjected to a one hour melting operation. Similar differences in density of procelain prepared from unmelted and melted frits of the same composition and calcination occurred in the following compositions: 184-9 (2.23 to 2.24) vs. 184-10 (2.36 to 2.38), 195-7 (2.29 to 2.30) vs. 195-8 (2.37 to 2.38) and 198-11 (2.29) vs. 198-12 (2.36).

Also, melted frits of the same composition fire into porcelains with greater translucency than those that are merely calcined. For example, the melted frit 194-8 has a translucency of 0.20 to 0.25 which is significantly greater than the translucency of its unmelted counterpart, 194-7 (0.35 to 0.40).

TABLE XIX

Frit Calcination and Melt Conditions

| Frit No. | Calcination Conditions Peak Temp., °C. | Time, Hrs. | Range, °C. | Melt Conditions Peak Temp., °C. | Time, Hrs. | Range, °C. | Porcelain Density, g/cm$^3$ (range) |
|---|---|---|---|---|---|---|---|
| 167-3 | 930 | 2 | 725-930 | | | | 2.28-2.30 |
| 183-11+ | 875 | 2 | 700-875 | 1354 | 1 | 1196-1354 | 2.37-2.38 |
| 184-9 | 950 | 1 | 700-950 | | | | 2.23-2.24 |
| 184-10 | 950 | 1 | 700-950 | 1346 | 1 | | 2.36-2.38 |
| 185-8 | 900 | 3 | 725-900 | 1354 | 1 | 1205-1354 | 2.36-2.37 |
| 186-5 | 875 | 1 5/6 | 725-875 | 1344 | 1 | 1205-1344 | 2.36-2.37 |
| 187-9 | 1000 | 2 | 725-1000 | 1350 | 1 | 1206-1350 | 2.35 |
| 188-6 | 925 | 2 | 725-925 | 1350 | 2 | 1206-1350 | 2.34-2.35 |
| 190-8 | 1000 | 1 | 725-1000 | 1346 | 1 | 1198-1346 | 2.36 |
| 192-6 | 825 | 4 5/6 | 700-825 | 1301 | 1½ | 1296-1301 | 2.37 |
| 194-7 | 1000 | 1 | 700-1000 | | | | 2.23-2.26 |
| 194-8 | 1000 | 1 | 700-1000 | 1346 | 1 | 1201-1346 | 2.36-2.38 |
| 195-7 | 975 | 1 | 700-975 | | | | 2.29-2.30 |
| 195-8 | 975 | 1 | 700-975 | 1350 | 1 | 1206-1350 | 2.37-2.38 |
| 196-6 | 900 | 1 | 700-900 | 1352 | 1 | 1197-1352 | 2.37-2.38 |
| 197-6 | 900 | 4 | 723-900 | 1350 | 1 | 1200-1350 | 2.36-2.38 |
| 198-11 | 850 | 1 | 570-850 | | | | 2.29 |
| 198-12 | 850 | 1 | 570-850 | 1298 | 1 | 1206-1298 | 2.36 |
| 200-11 | 1000 | 2 | 700-1000 | 1355 | 2 | 1205-1355 | 2.35-2.36 |
| 201-10 | 875 | 3 5/6 | 700-875 | 1343 | 1 | | 2.30-2.32 |
| 202-8 | 900 | 2 | 700-900 | 1352 | 1 | | 2.37-2.38 |
| 203-12 | 850 | 2 5/6 | 700-850 | 1353 | 1 | | 2.40 |
| 204-10 | 900 | 1 | 700-900 | 1355 | 1 | 1352-1355 | 2.37-2.38 |
| 205-18 | 800 | 2 | 675-800 | 1063-1122 | 1 | 850-1122 | 2.39-2.41 |
| 206-13 | 800 | 2 | 675-800 | 1301 | 1 | | 2.38-2.39 |
| 207-12 | 800 | 2 | 675-800 | 1352 | ½ | 1301-1352 | 2.38-2.42 |
| 208-12 | 875 | 1 | 700-875 | 1350 | ½ | 1200-1350 | 2.38-2.40 |
| 209-13 | 825 | 1 | 698-825 | 1352 | ½ | 1301-1352 | 2.40-2.41 |
| 210-12 | 850 | 1 | 700-850 | 1354 | 1 | | 2.42 |
| 211-4 | 925 | 1 | 725-925 | 1355 | 2 | 1205-1355 | 2.38-2.39 |
| 212-9 | 875 | 1 | 700-875 | 1350 | 2 | 1204-1350 | 2.27-2.29 |
| 213-3 | 750 | 1 | 700-750 | 1130 | 2 | 800-1130 | 2.28-2.30 |
| 214-6 | 875 | 1 | 700-875 | 1389 | ½ | 1354-1389 | 2.27-2.29 |
| 215-5 | 875 | 1 | 700-875 | 1380 | 1 | 1206-1380 | 2.27-2.30 |
| 216-3 | 950 | 1 | 725-950 | 1350-1380 | 1 | 1202-1380 | 2.39 |
| 228-3,4 | 900 | 1 | 675-900 | 950 | ½ | | 2.34-2.37 |

TABLE XIX-continued

| | Frit Calcination and Melt Conditions | | | | | | Porcelain |
|---|---|---|---|---|---|---|---|
| | Calcination Conditions | | | Melt Conditions | | | Density, |
| | Peak | | | Peak | | | |
| Frit No. | Temp., °C. | Time, Hrs. | Range, °C. | Temp., °C. | Time, Hrs. | Range, °C. | g/cm³ (range) |
| 229-3,4 | 1000 | 1 | 675–1000 | 1100 | ½ | | 2.30–2.34 |
| 231-3,4 | 925 | 1 | 675–925 | 1025 | 1 | 950–1025 | 2.37–2.38 |
| 235-3 | 1000 | 1 | 675–1000 | | | | 2.34–2.37 |
| 244-7,8 | 900 | 1 | 650–900 | 1047 | ½ | | 2.36–2.38 |
| 245-2,3 | 875 | 1 | 675–875 | 1100 | ½ | | 2.35–2.38 |
| 263-2,3 | 900 | 1 | 675–900 | 1052 | 1 | 900–1052 | 2.34–2.36 |

+An underlined number signifies that the frit was melted during the heat treatment sequence denoted by that number.

TABLE XX

Experimental Porcelain Properties

| Frit No. | Fusion Temp., °C. | Translucency, $C_{0.70}$ | Solubility, mg/cm² | Flexure Strength, kg/cm² | Deformation Temp., °C. | Coefficient of Thermal Expansion 23 to 400° C., × $10^{-6}$/°C. |
|---|---|---|---|---|---|---|
| 167-3 | 914–917 | 0.30–0.35 (917)+ | 0.135 (917)+ | 799 (916)+ | 637 (915)+<br>611 (916)<br>614 (917) | 8.54#<br>8.66<br>8.09 |
| 183-11** | 839 | 0.20–0.25 (846) | 0.798 (846) | n.d. | 501 (851) | 10.95 |
| 184-9 | 904 | 0.35–0.40 (910) | 0.447 (910) | 787 (908)<br>832* (910) | 563 (910) | 11.34 |
| 184-10 | 840 | 0.15–0.20 (840) | 0.613 (840) | n.d. | 554 (840) | 11.33 |
| 185-8 | 816 | 0.15–0.20 (850) | 1.421 (850) | 619 (816) | 579 (850) | 10.25 |
| 186-5 | 802 | 0.20–0.25 (802)<br>0.20–0.25 (807) | 3.664 (802)<br>2.963 (807) | 973 (802)<br>607 (806) | 567 (802)<br>570 (806) | 12.03<br>11.71 |
| 187-9 | 917 | 0.20–0.25 (918) | 0.616 (918) | 824 (920) | 620 (917) | 10.67 |
| 188-6 | 875 | 0.15–0.20 (900) | 0.789 (900) | 958 (875)<br>597 (897)<br>958 (900) | 623 (900) | 9.60 |
| 190-8 | 862 | 0.20–0.25 (880) | 0.636 (880) | 456 (862)<br>537 (880) | 558 (880) | 11.63 |
| 192-6 | 804 | 0.20–0.25 (802) | 2.582 (802) | 734 (822) | 549 (802) | 11.66 |
| 194-7 | 908 | 0.35–0.40 (923) | 0.481 (923) | 757* (919)<br>860* (922)<br>746* (924) | 578 (923) | 12.90 |
| 194-8 | 878 | 0.20–0.25 (885) | 0.720 (885) | 922 (885) | 563 (880)<br>567 (880)<br>567 (885) | 12.97<br>13.33<br>12.04 |
| 195-7 | 861 | 0.35–0.40 (897) | 0.948 (897) | 1126* (895)<br>1007* (895) | 583 (897) | 13.26 |
| 195-8 | 871 | 0.20–0.25 (883) | 0.778 (883) | 811 (871)<br>771 (881) | 572 (882) | 12.83 |
| 196-6 | 822 | 0.20–0.25 (830) | 1.746 (830) | 777 (827) | 571 (830) | 11.60 |
| 197-6 | 828 | 0.20–0.25 (831)<br>0.20–0.25 (874) | 1.505 (831)<br>1.693 (874) | 632 (829)<br>740 (871) | 579 (870) | 11.00 |
| 198-11 | 781 | 0.35–0.40 (780) | 1.436 (780) | 941 (790)<br>979 (781) | 570 (780) | 13.50 |
| 198-12 | 773 | 0.20–0.25 (783) | 0.930 (783) | n.d. | 556 (783) | 10.96 |
| 200-11 | 889 | 0.20–0.25 (907) | 0.819 (907) | 610 (889) | 598 (907) | 10.45 |
| 201-10 | 814 | 0.20–0.25 (871) | 1.910 (871) | 759 (814)<br>757 (869) | 551 (869) | 13.68 |
| 202-8 | 823 | 0.20–0.25 (838) | 1.210 (838) | 951 (823)<br>770* (834) | 545 (837) | 14.28 |
| 203-12 | 809 | 0.25–0.30 (852) | 0.954 (852) | 988 (809)<br>899* (851)<br>642* (852)<br>986* (864) | 562 (852) | 11.41 |
| 204-10 | 800 | 0.20–0.25 (833) | 0.764 (833) | 726 (800)<br>965* (827) | 558 (828) | 11.43 |
| 205-18 | 810 | 0.20–0.25 | 0.935 | 931 (810) | 565 (821) | 13.76 |

TABLE XX-continued
Experimental Porcelain Properties

| Frit No. | Fusion Temp., °C. | Trans-lucency, $C_{0.70}$ | Solubility, mg/cm² | Flexure Strength, kg/cm² | Deformation Temp., °C. | Coefficient of Thermal Expansion 23 to 400° C., $\times 10^{-6}/°C.$ |
|---|---|---|---|---|---|---|
| 206-<u>13</u>** | 791 | 0.20–0.25 (814) (802)+ | 0.915 (814) (802)+ | 664 (802)+ | 570 (802)+ 575 (802) | 11.13# 10.95 |
| 207-<u>12</u> | 790 | 0.20–0.25 (822) | 0.461 (822) | 750* (802) | 651 (822) | 12.13 |
| 208-<u>12</u> | 777 | 0.20–0.25 (777) | 0.695 (777) | 914 (774) | 550 (777) | 12.58 |
| 209-<u>13</u> | 814 | 0.20–0.25 (837) | 0.795 (837) | 789 (814) 678 (837) | 528 (837) | 13.25 |
| 210-<u>12</u> | 824 | 0.20–0.25 (879) | 0.897 (879) | 807 (879) | 563 (878) | 12.95 |
| 211-<u>4</u> | 889 | 0.15–0.20 (885) 0.20–0.25 (901) | 0.151 (885) 0.130 (901) | 918 (889) 924 (899) 767 (899) | 624 (890) n.d. (899) | 8.81 8.40 |
| 212-<u>9</u> | 926 | 0.20–0.25 (930) 0.20–0.25 (932) | 0.003 (930) 0.004 (932) | 900 (926) 881 (931) 972 (931) | 622 (926) n.d. (943) | 6.07 5.66 |
| 213-<u>3</u> | 899 | 0.20–0.25 (899) 0.20–0.25 (908) | 0.002 (899) 0.001 (908) | 1063 (899) 1070 (909) | 610 (895) 576 (907) 567 (910) | 6.61 6.33 5.93 |
| 214-<u>6</u> | 912 | 0.20–0.25 (911) 0.20–0.25 (920) 0.15–0.20 (920) | 0.000 (911) 0.000 (920) 0.002 (920) | 1116 (912) 876 (920) | 613 (914) 601 (920) | 6.42 5.17 |
| 215-<u>5</u> | 923 | 0.20–0.25 (931) | 0.003 (923) 0.003 (931) | 764 (923) | 613 (922) 627 (923) 612 (930) n.d. (943) | 6.19 5.87 5.65 5.04 |
| 216-<u>3</u> | 948 | 0.20–0.25 (948) | 0.164 (948) | 827 (948) 596 (948) | 612 (948) | 9.62 |
| 228-<u>3</u>,4 | 822 | 0.20–0.25 (822) | 0.849 (822) 0.880 (846) | 1138 (825) | 531 (848) | 12.82 |
| 229-<u>3</u>,4 | 926 | 0.20–0.25 (930) | 0.298 (930) | 810 (925) | 569 (931) | 12.07 |
| 231-<u>3</u>,4 | 921 | 0.20–0.25 (921) | 0.181 (921) 0.162 (931) | 425 (921) | 622 (918) | 12.63 |
| 235-3 | 914–915 | 0.30–0.35 (914) | 0.265 (914) 0.206 (926) | 538 (916) 592 (918) | 607 (915) | 12.61 |
| 244-<u>7</u>,8 (blisters) | 778–782 | 0.20–0.25 (782) | 1.352 (782) | 969 (788) 922 (781) 776 (792) | 556 (782) | 13.42 |
| 245-<u>2</u>,3 | 938–939 | 0.15–0.20 (939) | 0.014 (939) 0.003 (964) | 821 (938) 953 (939) | 650 (939) | 8.19 |
| 263-<u>2</u>,3 | 877–880 | 0.20–0.25 (878) | 0.534 (878) 0.489 (908) | 999 (877) 986 (880) | 556 (877) | 13.50 |

**Underlined number signifies that the frit was melted during the heat treatment sequence denoted by that number.
+Number in parentheses ( ) was the peak temperature at which the specimen was fired in air for 12 minutes.
Specimen temperature is the same as specimen listed indeformation temperature column.
*Specimen was ground to nonstandard dimensions. Bar was less thick and less wide than normal.

In fact, all melted frits, with the exception of 203-12, fire into porcelains with translucencies greater than 0.25. This is a greater translucency than most of the commercial body and enamel porcelains that have been examined (Table XVII, B). However, the 0.30 to 0.40 translucency of porcelains made from unmelted frits appears satisfactory for making any dental shade.

In addition, melted frits frequently fuse lower than unmelted frits of the same calcine and formulation; e.g., unmelted frit 184-9 (904° C.) and melted frit 184-10 (840° C.), again unmelted frit 194-7 (908° C.) and 194-8 (878° C.) and 198-11 (781° C.) and 198-12 (773° C.). However, unmelted frit 195-7 (861° C.) fuses 10° C. lower than melted frit 195-8 (871° C.).

With respect to commercial porcelains, several of the experimental frits are stronger than the strongest commercial metal-ceramic porcelains. Specifically, Neydium V body, B-1 and incisal, B-1 porcelains have flexure strengths that range from 868 to 1048 kg/cm$^2$. But the flexure strengths of unmelted frits 195-7 and 198-11 and melted frits 202-8, 203-12, 205-18, 208-12, 228-3, 4, and 263-2, 3 all appear to approximate or exceed the strength of the Neydium porcelains. Significantly, all of these frits fuse at temperatures much lower than the 1002° and 1004° C. necessary for the Neydium porcelains. Also, none of these experimental frits exhibit weight loss due to solubility greater than 1.44 mg/cm$^2$. This is less than one-third the solubility of the Neydium porcelains.

The commercial porcelain tested with highest 23–400° C. coefficient of expansion is maturely fired Will-Ceram body (B-1, 1977), 13.62×10$^{-6}$/° C. However, the deformation temperature of this porcelain is among the highest values obtained on commercial porcelains, 660° C.

Several experimental porcelains greatly exceed the 23–400° C. coefficient of expansion of mature Will-Ceram body porcelain, 13.62×10$^{-6}$/° C. These porcelains, 201'-10, 202-8 and 205-18 are all tested in the overfired condition and give 23–400° C. coefficients of 13.68, 14.28 and 13.76×10$^{-6}$/° C. The highest expanding of these, 202-8, gives, in a mature fire, a specimen with a flexure strength of 951 kg/cm$^2$ which equals strengths achieved in mature fires of the Will-Ceram body, 833 to 928 kg/cm$^2$. This 202 porcelain has a deformation temperature of only 545° C. Therefore this porcelain appears to be very suitable for very high expanding alloys. Also, its fusion temperature is very low, 823° C., and its translucency is high enough, 0.20 to 0.25, to give considerable latitude for shade development. Its solubility is not exceptionally low for the experimental porcelains, 1.210 mg/cm$^2$, but much less than Neydium's body porcelains, 4.872 to 6.182 mg/cm$^2$.

EXAMPLE 7

A gel is prepared by dissolving in 100 cc of a solution of 70 wt % nitric acid and water the following substances in grams: $H_3BO_3$, 0.666; $K_2CO_3$, 4.032; $Na_2CO_3$, 3.956; $Li_2CO_3$, 0.609. A mixture of 46.4 cm$^3$ Ludox 130 M (DuPont de Nemours and Co., Wilmington, Del.) and 6.85 cm$^3$ 5025 alumina sol (Hammil and Gillespie, New York, N.Y.) is then added quickly to the above solution under rapid stirring in a 200 cm$^3$ narrow neck beaker.

Excess water is evaporated from the above solution on a hot plate with constant mixing until a gel is formed. In the early stages of gelling the solution is mixed with a teflon-coated magnetic stirrer at a low temperature setting. As viscosity increases, stirring is continued manually with a large porcelain spatula with a hot plate surface temperature no higher than 150° C.

When a gel is formed, the gel is placed in a covered 2000 cc beaker and transferred to a forced air oven at 180° to 200° C. for 24 to 48 hours. The dried gel is then placed in a number 10 wide mouth crucible and heated in a Lindberg muffle furnace for one hour at 500° C., one hour at 600° C., and one hour at 700° to 750° C.

The precalcined frit is stage ground in a mullite mortar to pass through a 40-mesh screen and placed in a porcelain crucible. The crucible is reinserted in the muffle furnace at 700° C. for one hour. The calcination temperature is increased in steps of 25° C. to 1000° C. with firing time at each step of one hour. After each step the sample is air quenched. Calcination is complete when the frit is calcined at 1000° C. for one hour.

The calcined frit is then melted in platinum foil in a muffle furnace at 1346° C. for one hour. After melting, the frit is water quenched and stage ground through a 140-mesh screen. The resulting frit has the following composition in weight percent: $SiO_2$, 59.76; $Al_2O_3$, 17.51; $B_2O_3$, 1.50; $K_2O$, 10.99; $Na_2O$, 9.25; and $Li_2O$, 0.99.

The above examples illustrate that gel route prepared porcelain frits can attain or surpass the performance of current commercial dental porcelains. Aesthetic porcelains can be prepared by a gel route which equal or exceed the strength of many commercial low-fusing porcelains. Furthermore, particles of gel route prepared frit have the same composition and phase constitution. Therefore, gel route prepared frits can exhibit the even fluxing in all size ranges during the fire required for porcelain form retention. Also, gel route procedures permit the ready formulation of wider compositional variations than current porcelain fritting procedures. The incorporation of fillers is particularly easier by the gel route; these dispersed constituents can be wetted more effectively in a sol than in a viscous molten frit. Color shade and other quality-control maintenance procedures are potentially superior with this new fritting procedure. Experimental porcelains developed with low solubility and lower fusion points than current commercial porcelains make possible the use of cheaper or more ductile alloy dental restorative substrates which formerly could not be used because of discoloration of the porcelain, sag or oxidation. The possibility of making low-fusing strengthening glazes for metal-ceramic construction has also been demonstrated.

An additional advantage of porcelain frit prepared by the gel route is that dissolved rare earth constituents can be put into a high state of dispersion in the porcelain frit. Current procedures of digesting the rare earth oxides in the frit by fusion can give variable degrees of dispersion, especially when the rare earth is refractory, which, because these oxides when incompletely fritted have high refractive indices in any incompletely dissolved form, can lead to excess opacification.

In contrast to the fabrication of dental porcelain restorations from traditional frits, the gel route prepared frits potentially allow the making of porcelains that can be driven by heat treatment away from the vitreous state into a more submicrocrystalline, glass-ceramic-like state. This appears possible by gel route fritting because more refractory components, such as $ZrO_2$, can be incorporated in higher concentration in the vitreous state by gel route procedures than by current conventional methods. In general, the more refractory components have been observed to be very susceptible to devitrification in the fusion of gel prepared porcelains.

The gel route prepared porcelains have application also in such diverse fields as manufacture of electrical components and fine art materials.

It should be understood that the foregoing disclosure emphasizes certain specific embodiments of the invention and that all modifications or alternatives equivalent thereto are within the spirit or scope of the invention as set forth in the appended claims.

What is claimed is:

1. A method of preparing a dental porcelain article which comprises preparing a dental porcelain frit by the process comprising:
   (a) preparing a sol comprising in weight percent based on total solids content, 55-80% silica, 5-20% alumina, 12-40% flux constituents, and 0-7% additives, the 12-40% flux constituents comprising the solubilized oxides of boron, sodium, potassium, and lithium, the 0-7% additives comprising the solubilized oxides of calcium, magnesium, barium, strontium, zinc, tin, phosphorus, cesium, rubidium, yttrium, ytterbium, samarium, lanthanum, titanium, zirconium, terbium, thulium, cerium, europium and scandium with no single additive being present in an amount greater than 4%,
   (b) gelling the sol, and
   (c) calcining the gelled sol by heating it to calcination temperature to form a calcined frit, the frit being characterized by minimal microporosity and by a fusion temperature of 960° C. or less,
and then comminuting the frit, forming it into a dental porcelain article and firing it.

2. The method of claim 1 wherein the sol is peptized by acid.

3. The method of claim 1 wherein the sol is peptized by carbonate anions.

4. A method of preparing a dental porcelain article which comprises preparing a dental porcelain frit by the process comprising:
   (a) preparing a sol comprising in weight percent based on total solids content, 55-80% silica, 5-20% alumina, 12-40% flux constituents and 0-7% additives, the 12-40% flux constituents comprising solubilized oxides of boron, sodium, potassium, and lithium, the 0-7% additives comprising the solubilized oxides of calcium, magnesium, barium, strontium, zinc, tin, phosphorus, cesium, rubidium, yttrium, ytterbium, samarium, lanthanum, titanium, zirconium, terbium, thulium, cerium, europium and scandium with no single additive being present in an amount greater than 4%,
   (b) gelling the sol,
   (c) precalcining the gelled sol by heating it at a moderate temperature,
   (d) comminuting the heated, gelled sol, and
   (e) calcining the comminute at a higher temperature to form a calcined frit, the frit being characterized by minimal microporosity and by a fusion temperature of 960° C. or less,
and then recomminuting the frit, forming it into a dental porcelain article and firing it.

5. The method of claim 1 or 4 wherein the sol comprises, in weight percent based on total solids content, 55-70% silicon dioxide, 5-18% aluminum oxide, 0-10% solubilized boric oxide, 2-15% solubilized sodium oxide, 2-18% solubilized potassium oxide, 0-18% solubilized lithium oxide, and 0-5% solubilized oxides of calcium, magnesium, barium, strontium, zinc, tin, phosphorus, cesium, rubidium, yttrium, ytterbium, samarium, lanthanum, titanium, tantanlum, zirconium, terbium, thulium, cerium, europium and scandium.

6. The method of claim 5 wherein the calcined frit comprises 69.0-72.3 mole % silicon dioxide, 4.9-11.9 mole percent aluminum oxide, 6.0-9.0 mole percent boric oxide, 4.9-5.2 mole percent potassium oxide, 4.4-4.6 mole percent sodium oxide, and less than 1.5 mole percent total of oxides of zirconium, calcium, magnesium, phosphorus and zinc.

7. The method of claim 5 wherein the calcined frit comprises 69-73 mole % silicon dioxide, 7.5-9.6 mole % aluminum oxide, 5.0-9.6 mole % boric oxide, 3.0-6.3 mole % potassium oxide, 2.8-4.5 mole % sodium oxide and 0.5-5.0 mole % lithium oxide.

8. The method of claim 5 wherein the sol further comprises fine particles selected from the group consisting of quartz, potash feldspar, nepheline syenite, beta alumina, pyrex fiber, fused quartz fiber, silica fiber, hydrated unfused alumina, glass frit, unfused alumina, fused alumina, mica, high-fusing porcelain frit, titanium, aluminum, silicon, and tantalum.

9. The method of claim 8 wherein the fine particles are quartz, potash feldspar, pyrex fiber, fused alumina or lepidolite mica.

10. The method of claim 1 wherein the calcination temperature is between about 700 and about 1,500° C.

11. The method of claim 4 wherein precalcination comprises:
    (a) heating the gelled sol at temperatures from about 90 to about 200° C. for up to 40 to 60 hours, and then
    (b) heating the gelled sol at temperatures from about 400 to about 700° C.

12. The method of claim 11 wherein precalcination comprises:
    (a) dessicating the gelled sol at 90° to 100° C. for 20 to 30 hours and then at 190° to 200° C. for 20 to 30 hours, then
    (b) defuming the gelled sol for one hour at each of 500°, 600° and 700° C.

13. The method of claim 4 wherein the comminution of the heated, gelled sol is effected by grinding.

14. The method of claim 4 wherein calcination comprises heating the comminuted, heated, gelled sol at temperatures from about 700° to about 1500° C.

15. The method of claim 14 wherein the calcination further comprises heating the comminuted, heated, gelled sol from an initial temperature of 725° C. at successive 25° C. intervals for one hour each with retention time at maximum calcination temperature varying from 1 to 61 hours.

16. The method of claim 1 comprising the additional sub-step of
    (d) melting the calcined frit, before comminuting the frit.

17. The method of claim 4 comprising the additional sub-step of
    (f) melting the calcined frit, before recomminuting the frit.

18. A dental porcelain frit prepared by the method comprising:
    (a) preparing a sol comprising in weight percent based on total solids content, 55-80% silica, 5-20% alumina, 12-40% flux constituents, and 0-7% additives, the 12-40% flux constituents comprising solubilized oxides of boron, sodium, potassium, and lithium, the 0-7% additives comprising the solubilized oxides of calcium, magnesium, barium, strontium, zinc, tin, phosphorus, cesium, rubidium, yttrium, ytterbium, samarium, lanthanum, titanium, zirconium, terbium, thulium, cerium, europium and scandium with no single additive being present in an amount greater than 4%,
    (b) gelling the sol,
    (c) precalcining the gelled sol by heating it at a moderate temperature,
    (d) comminuting the heated, gelled sol, and (e) calcining the comminute at a higher temperature to form a calcinate, the calcinate being characterized by minimal microporosity and by a fusion temperature of 960° C. or less.

19. A dental porcelain frit as in claim 18 wherein the sol comprises, in weight percent based on total solids content, 55-70% silicon dioxide, 5-18% aluminum oxide, 0-10% solubilized boric oxide, 2-15% solubilized sodium oxide, 2-18% solubilized potassium oxide, 0-18% solubilized lithium oxide, and 0-5% solubilized oxides of calcium, magnesium, barium, strontium, zinc, tin, phosphorus, cesium, rubidium, yttrium, ytterbium, samarium, lanthanum, titanium, tantalum, zirconium, terbium, thulium, cerium, europium and scandium.

20. A dental porcelain frit as in claim 19 wherein the sol further comprises fine particles selected from the group consisting of quartz, potash feldspar, nepheline syenite, beta alumina, pyrex fiber, fused quartz fiber, silica fiber, hydrated unfused alumina, glass frit, unfused alumina, fused alumina, mica, high-fusing porcelain frit, titanium, aluminum, silicon, and tantalum.

21. A dental porcelain frit as in claim 18 wherein precalcination comprises:
 (a) heating the gelled sol at temperatures from about 90° to about 200° C. for up to 40 to 60 hours, and then
 (b) heating the gelled sol at temperatures from about 400° to about 700° C.

22. A dental porcelain frit as in claim 18 wherein calcination comprises heating the comminuted, heated, gelled sol at temperatures from about 700° to about 1500° C.

23. A dental porcelain frit as in claim 18 prepared by a method further comprising the additional step of
 (f) melting the calcinate.

24. In a porcelain denture tooth prepared from porcelain frit, the improvement which comprises employing the dental porcelain frit of claims 18, 19, 20, 21, 22, or 23, therein.

25. In a jacket-crown reconstruction prepared from porcelain frit, the improvement which comprises employing the dental porcelain frit of claims 18, 19, 20, 21, 22, or 23, therein.

26. In a method for preparing an inlay reconstruction prepared from porcelain frit, the improvement which comprises employing the dental porcelain frit of claims 18, 19, 20, 21, 22, or 23, therein.

27. In a method for preparing a restorative construction prepared from porcelain frit coated over a metal or preformed alumina substrate, the improvement which comprises employing the dental porcelain frit of claims 18, 19, 20, 21, 22, or 23, therein.

28. A dental glaze prepared from the dental porcelain frit of claims 18, 19, 20, 21, 22, or 23.

* * * * *